(12) United States Patent
Degen et al.

(10) Patent No.: US 9,956,336 B2
(45) Date of Patent: May 1, 2018

(54) METHODS OF USING A FLUID MANAGEMENT SYSTEM

(71) Applicant: SEQUANA MEDICAL AG, Zug (CH)

(72) Inventors: Thomas Werner Degen, Birmensdorf (CH); Daniel Thomas Thommen, Steinhausen (CH); Noel L. Johnson, Saratoga, CA (US)

(73) Assignee: Sequana Medical AG, Zug (CH)

( * ) Notice: Subject to any disclaimer, the term of this patent is extended or adjusted under 35 U.S.C. 154(b) by 1196 days.

(21) Appl. No.: 14/077,005

(22) Filed: Nov. 11, 2013

(65) Prior Publication Data

US 2014/0066841 A1    Mar. 6, 2014

Related U.S. Application Data

(63) Continuation of application No. 13/397,498, filed on Feb. 15, 2012, now Pat. No. 8,585,635.

(51) Int. Cl.
*A61M 1/00*    (2006.01)
*A61M 1/28*    (2006.01)
*A61M 1/16*    (2006.01)

(52) U.S. Cl.
CPC ............ *A61M 1/28* (2013.01); *A61M 1/1676* (2014.02); *A61M 1/285* (2013.01); *A61M 1/287* (2013.01);
(Continued)

(58) Field of Classification Search
CPC ...... A61M 1/28; A61M 1/1676; A61M 1/287; A61M 2205/04; A61M 2205/3523;
(Continued)

(56) References Cited

U.S. PATENT DOCUMENTS 4,240,434 A    12/1980    Newkirk
4,610,658 A    9/1986    Buchwald et al.
(Continued)

FOREIGN PATENT DOCUMENTS

EP    0 980 685    2/2000
EP    1 362 605 A1    11/2003
(Continued)

OTHER PUBLICATIONS

PCT International Search Report and Written Opinion dated Mar. 18, 2013 in related PCT Application No. PCT/US2012/025188.
(Continued)

*Primary Examiner* — Rebecca E Eisenberg
(74) *Attorney, Agent, or Firm* — Foley & Lardner LLP; Christopher C. Bolten; Nicola A. Pisano

(57) ABSTRACT

An artificial liver system for treating liver failure includes a reservoir to provide albumin-containing dialysis fluid to the patient's peritoneum, an implantable device including a pump to pump the fluid from the peritoneum to the bladder via respective catheters, control circuitry, battery and transceiver; a charging and communication system configured to periodically charge the battery and communicate with the implantable device to retrieve data reflective of the patient's health; and monitoring and control software, suitable for use with conventional personal computers, for configuring and controlling operation of the implantable device and charging and communication system. The monitoring and control software allows a treating physician to remotely adjust the volume, time, and frequency with which fluid is pumped from the peritoneal cavity to the bladder based on the data reflective of the patient's health.

21 Claims, 14 Drawing Sheets

(52) U.S. Cl.
CPC . *A61M 2205/04* (2013.01); *A61M 2205/3523* (2013.01); *A61M 2205/50* (2013.01); *A61M 2205/52* (2013.01); *A61M 2205/8206* (2013.01); *A61M 2205/8243* (2013.01); *A61M 2209/088* (2013.01)

(58) Field of Classification Search
CPC .......... A61M 2205/50; A61M 2205/52; A61M 2205/8206; A61M 2205/8243; A61M 2209/088
See application file for complete search history.

(56) References Cited

U.S. PATENT DOCUMENTS

| | | | |
|---|---|---|---|
| 4,657,530 | A | 4/1987 | Buchwald et al. |
| 4,725,207 | A | 2/1988 | Buchwald et al. |
| 4,772,257 | A | 9/1988 | Hakim et al. |
| 5,011,472 | A | 4/1991 | Aebischer et al. |
| 5,037,385 | A | 8/1991 | O'Byrne |
| 5,397,354 | A | 3/1995 | Wilk et al. |
| 5,902,336 | A | 5/1999 | Mishkin |
| 5,944,684 | A | 8/1999 | Roberts et al. |
| 6,214,802 | B1 | 4/2001 | Nakamura et al. |
| 6,245,039 | B1 | 6/2001 | Brugger et al. |
| 6,264,625 | B1 | 7/2001 | Rubenstein et al. |
| 6,554,822 | B1 | 4/2003 | Holschneider et al. |
| 6,613,095 | B1 | 9/2003 | Levin |
| 6,656,227 | B2 | 12/2003 | Levin |
| 6,845,267 | B2 | 1/2005 | Harrison et al. |
| 6,911,014 | B2 | 6/2005 | Wentling et al. |
| 6,960,179 | B2 | 11/2005 | Gura |
| 7,169,303 | B2 | 1/2007 | Sullivan et al. |
| 7,311,690 | B2 | 12/2007 | Burnett |
| 7,909,790 | B2 | 3/2011 | Burnett |
| 8,012,118 | B2 | 9/2011 | Curtin et al. |
| 8,202,248 | B2 | 6/2012 | Burnett et al. |
| 8,394,048 | B2 | 3/2013 | Burnett |
| 8,398,577 | B2 | 3/2013 | Burnett |
| 2002/0123715 | A1* | 9/2002 | Sorenson ................ A61M 1/28 604/29 |
| 2003/0114787 | A1 | 6/2003 | Gura |
| 2003/0171710 | A1* | 9/2003 | Bassuk ............... A61M 31/002 604/67 |
| 2004/0049288 | A1 | 3/2004 | Levin |
| 2004/0098113 | A1 | 5/2004 | Forsell et al. |
| 2004/0147871 | A1* | 7/2004 | Burnett ............ A61M 5/14276 604/9 |
| 2005/0131340 | A1 | 6/2005 | Sorenson et al. |
| 2005/0273034 | A1 | 12/2005 | Burnett |
| 2006/0058731 | A1 | 3/2006 | Burnett et al. |
| 2007/0055197 | A1 | 3/2007 | Shakir |
| 2008/0230450 | A1* | 9/2008 | Burbank ............. A61M 1/1656 210/92 |
| 2009/0198174 | A1 | 8/2009 | Childers et al. |
| 2009/0318844 | A1 | 12/2009 | Burnett |
| 2010/0114012 | A1 | 5/2010 | Sandford et al. |
| 2010/0312163 | A1 | 12/2010 | Forsell |
| 2011/0184339 | A1 | 7/2011 | Tan |
| 2011/0184340 | A1 | 7/2011 | Tan et al. |
| 2012/0209085 | A1 | 8/2012 | Degen et al. |
| 2012/0209165 | A1 | 8/2012 | Degen et al. |

FOREIGN PATENT DOCUMENTS

| | | |
|---|---|---|
| JP | H04-327857 | 11/1992 |
| WO | WO-2006/023589 A2 | 3/2006 |
| WO | WO-2009/096854 A1 | 8/2009 |

OTHER PUBLICATIONS

Rosenblit et al., "Peritoneal-urinary drainage for treatment of refractory ascites: a pilot study," J. Vascular & Interv. Radiology, (Nov./Dec. 1998), 9(6):998-1005.

* cited by examiner

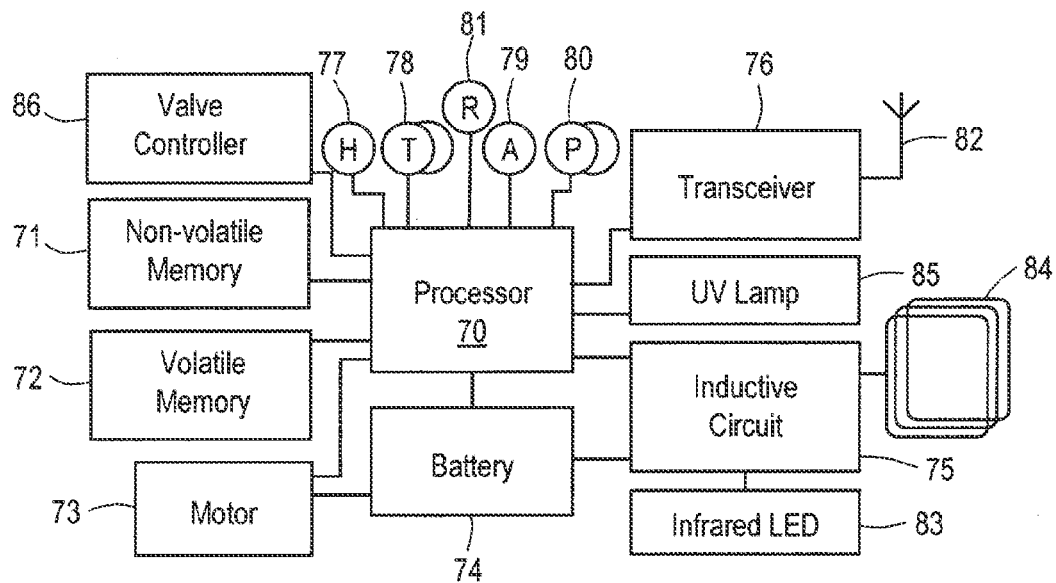
FIG. 4
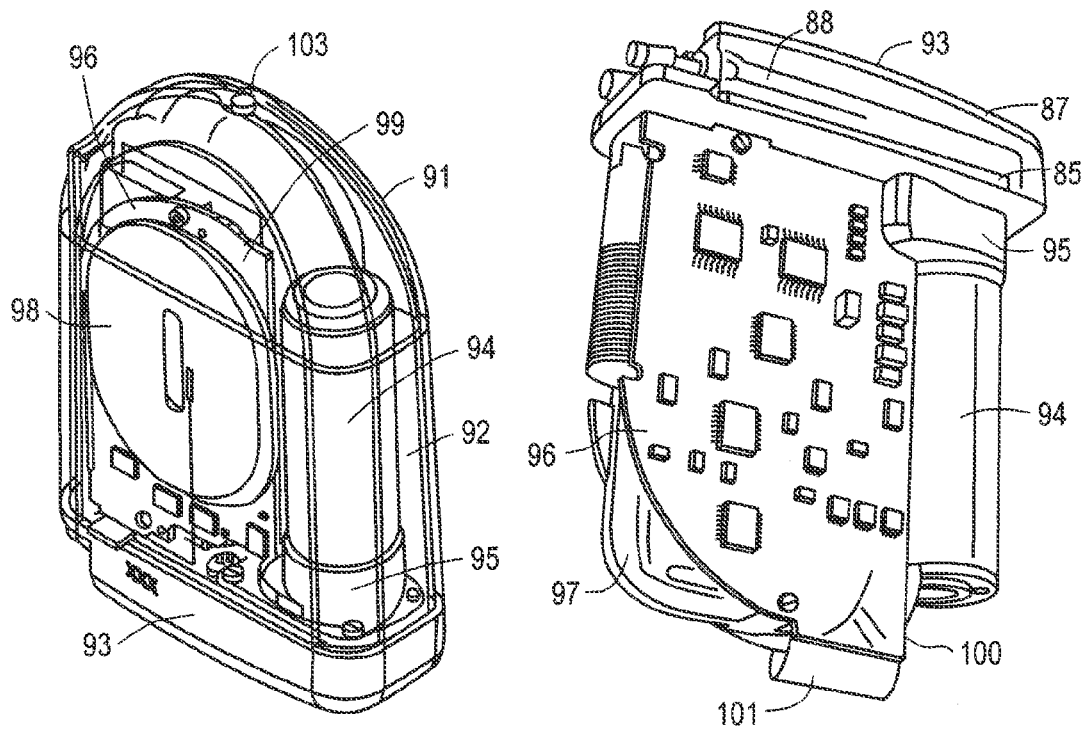
FIG. 5A
FIG. 5B

METHODS OF USING A FLUID MANAGEMENT SYSTEM

CROSS-REFERENCE TO RELATED APPLICATIONS

This application is a continuation of U.S. patent application Ser. No. 13/397,498, filed Feb. 15, 2012, now U.S. Pat. No. 8,585,635, issued Nov. 19, 2013, the entire contents of which is incorporated herein by reference.

I. FIELD OF THE INVENTION

This application relates to apparatus and methods for removing toxins and waste products from the body based on peritoneal dialysis.

II. BACKGROUND OF THE INVENTION

Liver failure is a syndrome caused by the incapacity of the liver to adequately perform its functions. Liver failure may be acute, e.g., caused by acute diseases such as acute viral or toxic hepatitis, or it may be chronic (Chronic Liver Failure, or "CLIF"), e.g., caused by alcoholism, hepatitis B or C, or fatty liver disease. CLIF is by far the most common presentation of liver failure, and typically is associated with cirrhosis, in which healthy liver tissue is replaced by scar tissue, and fails to adequately cleanse the blood of toxins and waste products. CLIF is typically associated with functional failure of several other organs, including the cardiovascular system, brain, kidneys, and adrenal glands, and immune defense mechanisms against endogenous and exogenous bacterial infections. In addition, patients with CLIF are susceptible to Acute on Chronic Liver Failure (AOCLIF), a complex syndrome in which an acute precipitating factor, such as infection or injury to the liver, causes the acute development of complications related to CLIF and failure in the function of other organs. The probability of survival of patients with CLIF is short, typically less than 3 years, and AOCLIF is the complication associated with the worst prognosis. Liver transplantation is therefore the treatment of choice in patients with advanced CLIF. Unfortunately, only a minority of patients may receive transplants because of the great imbalance between potential recipients and donors.

The mechanism of CLIF is complex and not related to the impairment of liver function alone, as is the case with other organ failures. Impairment of liver function is caused by the progressive destruction of liver tissue that reduces liver mass, and thus reduces the number of functional hepatocytes. The net effect of such a reduction is the impairment of synthetic and excretory function, which modifies the levels of several substances in blood and thus may detrimentally impact the function of multiple organs. Measurement of the blood concentration of these substances thus may be used as indicators of liver failure, e.g., an decrease in albumin or coagulation factors, and/or an increase in toxins such as ammonia or bilirubin. Hepatic encephalopathy may result from the accumulation of some of such toxins plus the activation of inflammatory pathways. Immune defense mechanisms may be impaired, causing an increased passage of viable bacteria and bacterial products (e.g., endotoxin) from the intestinal lumen into the systemic circulation, causing infections such as spontaneous bacterial peritonitis and/or systemic inflammatory response such as increased circulating levels of damaging cytokines. Destruction of liver mass may also activate regenerative mechanisms that promote the development of liver cancer, e.g., hepatocellular carcinoma. Liver cell necrosis also may lead to fibrosis disruption of the intrahepatic circulation and increase in hydrostatic pressure in the portal vein (referred to as portal hypertension), which may cause oesophageal varices that may rupture and manifest as gastrointestinal hemorrhage. Portal hypertension also may cause ascites, in which fluid chronically collects in the peritoneal cavity. As CLIF progresses there also may be changes in cardiovascular function, including arterial vasodilation, decrease in cardiac function, and increased release of a series of vasoconstrictor substances, such as renin and noradrenaline, that may cause renal failure secondary to renal vasoconstriction (hepatorenal syndrome) and may participate in the pathogenesis of multiorgan failure in AOCLIF.

Current therapies for CLIF have been developed for the complications associated with the syndrome, such as ascites, infections, encephalopathy, bleeding, and liver cancer. For example, hepatic encephalopathy may be treated with agents such as probiotics, antibiotics, and/or cathartics that decrease the generation of ammonia and other toxic substances in the gut and thus decrease the amount of toxins for the diseased liver to process. Treatment of circulatory dysfunction and renal failure may include administering albumin, a protein that binds to several toxins that cause vasodilations, which may improve cardiac function. Other therapies may be focused on measures that compensate for excessive fluid retention (e.g., administering diuretics to treat ascites); decrease pressure in the oesophageal varices (e.g., administering beta adrenergic blockers); eradicate the varices (e.g., banding of varices using endoscopy); kill infection-causing bacteria (e.g., administering antibiotics); and/or increase blood pressure (e.g., administering vasoconstrictors to treat circulatory dysfunction). Such approaches are reactive and predominantly directed at the active management of a patient with manifest complication(s).

Because the life expectancy of patients with CLIF is relatively short and because the availability of liver transplants is insufficient, a need has arisen to provide artificial means to cleanse the body of toxins and waste products, such as endogenous metabolites, which are known to be particularly critical in maintaining the function of the liver and other organs. Initial systems for doing so were developed in the 1970s, and were based on the traditional form of dialysis, in which a patient's blood was removed from the body, passed through a dialysis machine, and returned to the body. Although such systems showed some benefit, it was found that they were insufficiently able to remove water-insoluble, albumin-bound toxic substances. One step forward in this regard was the introduction of charcoal hemoperfusion, but biocompatibility problems limited the use of such systems.

Presently, there are two general categories of Artificial Liver Support Systems ("ALSS"), namely bioartificial and artificial livers. Both are based on connecting the patient circulatory system to an extracorporeal circuit, in which the blood or the plasma of the patient is circulated through bioreactors that contain liver cells (bioartificial) or through capillaries in columns with dialysis fluid (artificial) that may be enriched with albumin, which has a high capacity to bind water-insoluble toxic substances. Although bioartificial livers have shown to improve survival in some groups of patients, they are very complex and expensive, and have the limitation of requiring viable liver cells during the procedure.

Artificial ALSS systems, such as MARS (Molecular Adsorbent Recirculating System) and Prometheus, utilize a dialysate solution containing albumin. The MARS system is widely used. In addition to conventional dialysis, MARS provides hemodialysis against a dialysate solution that contains albumin using a membrane that is permeable to small and middle molecular weight substances. Water soluble and insoluble substances accumulated in the blood are transferred along a concentration gradient to the secondary circuit that contains the albumin dialysis solution. Those that are water insoluble are transiently bound by albumin in the secondary circuit, and subsequently by resins and charcoal absorbent columns, which regenerates the albumin for use in binding additional water insoluble substances. Water-soluble substances are removed by the conventional dialysis.

Although numerous studies of ALSS in patients with AOCLIF have shown significant beneficial effects in cardiovascular function, hepatic encephalopathy and, in patients with renal failure, in blood urea and serum creatinine levels, a substantial survival benefit has not been shown. This may be because the disease has progressed too far by the time ALSS treatment has begun. Additionally, because ALSS involves extracorporeal blood processing, it requires the use of catheters, anticoagulation medication, and close clinical control, and therefore requires hospitalization. This may significantly increase the cost of treating the patient and reduce his quality of life, thus potentially reducing compliance.

Alternative approaches have been developed for cleansing the blood of toxins and waste products based on peritoneal dialysis, in which dialysate is introduced into the patient's peritoneal cavity. For example, U.S. Pat. No. 7,169,303 to Sullivan describes passing dialysate into a patient's peritoneal cavity, then withdrawing the dialysate from the peritoneal cavity and passing the withdrawn dialysate through an extracorporeal treatment system that includes a sorbent suspension for toxin removal. Although such a method may avoid the need to withdraw blood as in ALSS, it still may be used only at too late a stage in the progression of CLIF and still may require hospitalization because of its extracorporeal nature.

U.S. Pat. No. 8,012,118 to Curtin describes a wearable dialysis system for removing uremic waste metabolites and fluid from a patient suffering from renal disease, in which a small external pump continuously recirculates peritoneal dialysis solution between the peritoneal cavity, where uremic waste metabolites diffuse through the peritoneal membrane into the dialysis solution, and a replaceable cartridge that cleans the solution and that may be replaced when the various layers become saturated. Curtin describes that albumin can be added to the peritoneal dialysis solution in the removal of protein-bound toxins and that a bacterial filter may be used to remove bacterial contamination from the solution. Curtin further describes that the fluid loop includes a replaceable drain container that drains excess fluid that has been added to the peritoneal dialysis solution through osmosis from the patient's body. A plurality of hollow fiber membranes may be connected to the patient's blood stream via vascular grafts to remove excess fluid from the blood stream, and that such excess fluid may be drained to the patient's bladder.

Although the system described in Curtin may avoid the need for frequent hospitalization and improve convenience to the patient, the dialysis is still performed extracorporeally, requires the periodic replacement of cartridges and the periodic draining of excess fluid that has been added to the peritoneal solution through osmosis from the patient's body, and is susceptible to contamination by pathogens not captured by the bacterial filter, either because the pathogens are sufficiently small or do not circulate through the filter. Moreover, as for ALSS and previously-known peritoneal dialysis, the system of Curtin may not be implemented until a patient is at a more advanced stage of CLIF and thus less likely to achieve an improved life expectancy. Further, the treating physician's involvement may be relatively infrequent because it is based on office visits, so the physician may not be aware of—nor in a position to immediately treat—a change in the patient's health.

In view of the above-noted drawbacks of previously-known systems, it would be desirable to provide methods and apparatus for treating CLIF using an implantable device having a minimum number of parts requiring replacement, avoids the need for the patient to handle multiple types of fluid, and reduces the risk of infection, allows for continual physician involvement, and that may be used at earlier stages of CLIF and thus reduce complications associated with CLIF.

III. SUMMARY OF THE INVENTION

The present invention overcomes the drawbacks of previously-known systems and methods of treating liver failure by providing an artificial liver system that automatically and autonomously provides albumin-containing dialysate into a patient's peritoneal cavity, and then removes the dialysate with toxins and waste products therein to the patient's bladder, with reduced burden on the patient. The artificial liver system of the present invention also periodically or continually provides data reflective of the patient's health to the treating physician, who may remotely adjust the patient's dialysis treatment based on changes in the patient's health.

The artificial liver system of the present invention preferably comprises a reservoir containing a peritoneal dialysis fluid comprising albumin and configured to provide the peritoneal dialysis fluid to the patient's peritoneum; a peritoneal catheter configured for implantation in the patient's peritoneum; and a bladder catheter configured for implantation in the patient's bladder. The system further preferably comprises an implantable device including a pump, a controller, a battery and a transceiver, and being configured to pump the peritoneal dialysis fluid in the peritoneum to the patient's bladder via the peritoneal catheter and the bladder catheter; a charging and communication system configured to periodically charge the battery of, and communicate with, the implantable device; and monitoring and control software, suitable for use with a conventional personal computer, for configuring and controlling operation of the implantable device and charging and communication system. Preferably, the monitoring and control software is available only to the treating physician, such that the patient generally interacts with the implantable device only via the charging and communication system for purposes of recharging the implantable device. The monitoring and control software may be used to monitor the patient's health and to adjust the parameters of the dialysis treatment if needed, e.g., by increasing or decreasing the flow rate of dialysate into or out of the peritoneal cavity, the volume of dialysate, the frequency of pumping, and/or the time the fluid remains within the peritoneal cavity, so as to reduce the likelihood of the patient's CLIF worsening and potentially improve the health of the patient's liver and other organs.

In some embodiments, the reservoir is configured for external use. Optionally, the system includes an external pump configured to facilitate flow of the peritoneal dialysis fluid from the reservoir to the patient's peritoneum. The system may include a belt configured to secure the reservoir to the patient's body, and the reservoir may include at least one pouch arranged along the length of the belt. A reservoir catheter may be coupled to the dialysate reservoir and to the implantable device, the pump further being configured to pump the peritoneal dialysis fluid from the reservoir to the patient's peritoneum via the reservoir catheter and the peritoneal catheter. First and second valves may be provided in operable communication with the implantable device, the second valve being configured to be actuated so as to prevent flow from the bladder to the peritoneum when the peritoneal dialysis fluid is pumped from the reservoir to the peritoneum, the first valve being configured to be actuated so as to prevent flow from the peritoneum to the reservoir when the peritoneal dialysis fluid is pumped from the peritoneum to the bladder.

In other embodiments, the dialysate reservoir is configured for internal implantation and comprises a port configured to receive fresh peritoneal dialysis fluid. A reservoir catheter may be coupled to the dialysate reservoir and to the implantable device, the pump further being configured to pump the peritoneal dialysis fluid from the reservoir to the patient's peritoneum via the reservoir catheter and the peritoneal catheter. The system may include first and second valves in operable communication with the implantable device, the second valve being configured to be actuated so as to prevent flow from the bladder to the peritoneum when the peritoneal dialysis fluid is pumped from the reservoir to the peritoneum, the first valve being configured to be actuated so as to prevent flow from the peritoneum to the reservoir when the peritoneal dialysis fluid is pumped from the peritoneum to the bladder.

The charging and communication system may further include a handpiece housing the second controller, the second transceiver, the second inductive charging circuit and a second battery; and a base containing circuitry for charging the second battery. The second inductive circuit may include a coil, and the handpiece may be configured to facilitate externally positioning the handpiece in alignment with the implantable device.

The first controller may be programmed to automatically activate the motor and gear pump to move fluid during predetermined time periods and in predetermined volumes responsive to operational parameters communicated by the monitoring and control software. The first controller may be programmed to automatically activate the motor and gear pump to move fluid at high flow rates during pumping, and thereby clean the inflow and outflow catheters to reduce the risk of clogging. The first controller may be programmed to periodically activate the motor and gear pump in a tick mode to reduce potential clogging, substantially without moving fluid through the outflow catheter. The first controller may be programmed to operate the motor and gear pump in a jog mode to unblock the gear pump, wherein the motor is rapidly alternated between forward and reverse directions.

The implantable device further may include sensors configured to measure respiratory rate, fluid temperature, fluid viscosity, fluid pressure in the peritoneum, and fluid pressure in the bladder, and may be configured to store data corresponding to measurements made by the sensors. The charging and communication system may be configured to wirelessly download the data stored on the implantable device to a memory disposed within the charging and communication system via the first and second transceivers. The monitoring and control software may be configured to periodically communicate with the charging and communication system, using either a wired or wireless connection, to retrieve the data stored in the memory. The monitoring and control software further may be configured to detect a change in the patient's health based on an increase in at least one of the measured respiratory rate, fluid temperature, or fluid viscosity above a predefined threshold, and to visually display to a user information about the detected change in the patient's health. The monitoring and control software may be further configured to modify operational parameters of the implantable device based on the detected change in the patient's health. The modified operational parameters may include at least one of: a volume of the peritoneal dialysis fluid, a time period for which the peritoneal dialysis fluid is permitted to remain within the patient's peritoneum, and a frequency with which peritoneal dialysis fluid is removed from the patient's peritoneum to the bladder. The detected change in the patient's health may be, for example, an infection or a change in liver function.

In some embodiments, the implantable device includes an ultraviolet (UV) lamp, and the first controller is configured to expose the peritoneal dialysis fluid to light from the UV lamp for a sufficient amount of time to inhibit the growth of colonies of one or more pathogens.

IV. BRIEF DESCRIPTION OF THE DRAWINGS

FIG. 4 is a schematic diagram of the electronic components of an exemplary embodiment of the implantable device of the present invention.

FIGS. 5A and 5B are, respectively, a perspective view of the implantable device of the present invention with the housing shown in outline and a perspective view of the obverse side of the implantable device with the housing and low water permeable filler removed.

FIGS. 6A, 6B, 6C and 6D are, respectively, an exploded perspective view of the drive assembly of the implantable device; front and plan views of the upper housing; and a perspective view of the manifold of an exemplary embodiment of the implantable device.

V. DETAILED DESCRIPTION OF THE INVENTION

Embodiments of the present invention provide artificial liver systems and methods for treating liver failure, in particular CLIF. The artificial liver systems and methods are based on peritoneal dialysis, in that a dialysate is introduced into the peritoneal cavity, where toxins and waste products diffuse out of the body and into the dialysate via the peritoneal membrane. However, the present systems and methods pump the dialysate to the patient's bladder by a subcutaneously implantable pump for evacuation with the urine, rather than pumping the dialysate to an external device. As such, the convenience to the patient is greatly improved because they need not visit a hospital or other facility to receive a sophisticated extracorporeal dialysis process, e.g., as in U.S. Pat. No. 7,169,303 to Sullivan, and need not wear an external pump and replaceable cartridge as in U.S. Pat. No. 8,012,118 to Curtin. Preferably, the peritoneal dialysate is enriched with albumin, which may bind to water insoluble or poorly water soluble toxins or waste products. Additionally, the present systems and methods may also reduce the patient's blood volume and remove ascites, thus increasing the patient's comfort and reducing the likelihood that the patient will develop one or more complications associated with CLIF.

As described in greater detail below, preferred embodiments include an implantable device including a pump that is specially configured to move fluid out of the peritoneal cavity and into the bladder, and that includes a plurality of sensors for monitoring and recording operating parameters relevant to the health of the patient. An externally held charging and communication system periodically charges and communicates with the implantable device, and downloads from the device the recorded operating parameters. Monitoring and control software on the treating physician's computer receives the recorded operating parameters from the charging and communication system, and allows the physician to modify the operation of the implantable device based on the physician's perception of the patient's health as reflected in the recorded operating parameters. Optionally, the monitoring and control software may be configured to alert the physician as to a prediction or detection of infection based on the recorded operating parameters. The implantable device optionally may also include one or more ultraviolet (UV) lamps configured to inhibit infection.

System and Method Overview

Figure 1A:
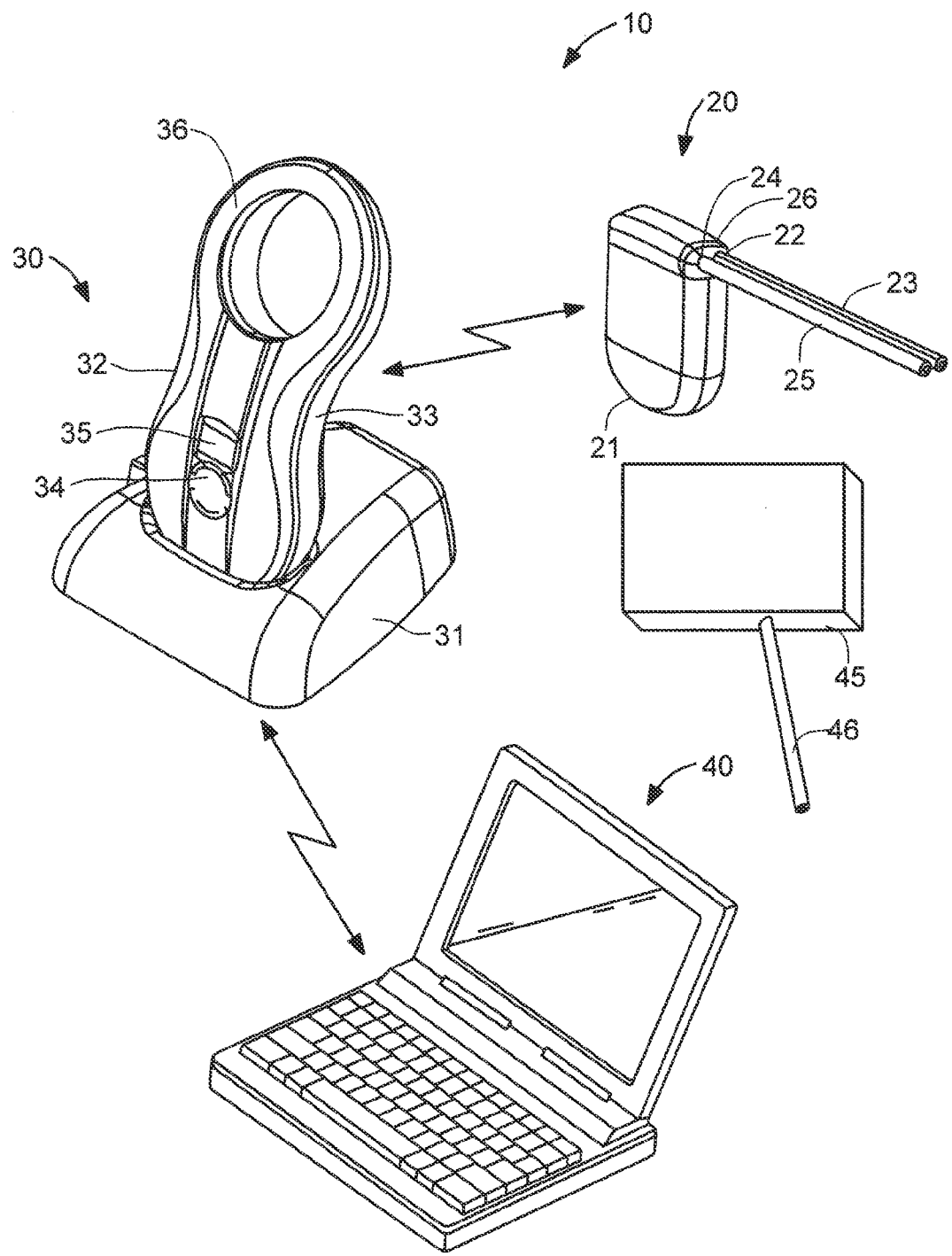
FIG. 1A is a perspective view of selected components of an exemplary artificial liver system constructed in accordance with a first embodiment of the present invention.

Referring to FIG. 1A, an overview of selected components of artificial liver system 10 of the present invention is provided. In FIG. 1A, components of the system are not depicted to scale on either a relative or absolute basis. Artificial liver system 10 comprises implantable device 20, external charging and communication system 30, software-based monitoring and control system 40, and peritoneal dialysate reservoir 45. In the illustrated embodiment, monitoring and control system 40 is installed and run on a conventional laptop computer used by the patient's physician. During patient visits, charging and communication system 30 may be coupled, either wirelessly or using a cable, to monitoring and control system 40 to download for review data stored on implantable device 20, or to adjust the operational parameters of the implantable device. Monitoring and control system 40 also may be configured to upload and store date retrieved from charging and communication system 30 to a remote server for later access by the physician or charging and communications system 30.

Implantable device 20 comprises an electromechanical pump having housing 21 configured for subcutaneous implantation. As described in further detail below with reference to FIG. 1B, implantable device 20 may include an electrically-driven mechanical gear pump having inlet port 22 coupled to peritoneal catheter 23 and outlet port 24 coupled to bladder catheter 25, and the peritoneal dialysis fluid is separately provided to the patient's peritoneum from reservoir 45. Peritoneal catheter 23 comprises a tube having a first (proximal) end configured to be coupled to pump inlet 23 and a second (distal) end configured to be positioned in the peritoneal cavity. Bladder catheter 25 comprises a tube having a first (proximal) end configured to be coupled to pump outlet 24 and a second (distal) end configured to be inserted through the wall of, and fixed within, a patient's bladder. In a preferred embodiment, both catheters are made of medical-grade silicone and include polyester cuffs at their distal ends (not shown) to maintain the catheters in position. Peritoneal catheter 23 and bladder catheter 25 are coupled to pump housing 21 using connector 26 configured to reduce the risk of improper installation and inadvertent disconnection, and may in addition include distinct cross-sections that reduce the risk of improper installation.

Reservoir 45 is configured to deliver albumin-containing peritoneal dialysis fluid (also referred to herein as dialysate, peritoneal dialysate, or fluid) to the patient's peritoneal cavity via catheter 46, which may have similar construction to the peritoneal catheter described further below with respect to FIGS. 2A-2B. In embodiments described further below with reference to FIG. 1B, the proximal end of catheter 46 may be configured to be removably coupled to an external reservoir 45 via an appropriate coupling allowing the patient to easily exchange a depleted reservoir for a fresh one, and the distal end of catheter 46 may configured for implantation in the patient's peritoneum, with a tissue cuff (not shown) to promote tissue ingrowth at the point at which catheter 46 crosses the patient's skin. The distal end of catheter 46 may have a plurality of holes or apertures defined therein, like those discussed below with reference to FIG. 2B. Reservoir 45 may deliver the peritoneal dialysis fluid to the peritoneal cavity by any suitable mechanism, For example, an external pump may be used to facilitate fluid flow from the reservoir 45 to the peritoneum, or the reservoir may be physically raised above the level of the peritoneum such that gravity draws the peritoneal dialysis fluid into the peritoneum via catheter 46. In other embodiments described below with reference to FIGS. 1C-1E, the distal end of reservoir catheter 46 instead may be attached to the inlet port 22 of implantable device 20, and implantable device 20 may be configured to pump the peritoneal dialysis fluid from reservoir 45 into the peritoneal cavity via reservoir catheter 46 and peritoneal catheter 23. In such embodiments, reservoir 45 may be external or implantable, and implantable device 45 further may include one or more passive or active valves to prevent fluid from being pumped out of the bladder and into the peritoneum at the same time that fluid is pumped from the reservoir and into the peritoneum.

The composition of the dialysate may include, for example, electrolytes and albumin, in sufficient concentrations as to cause sufficient quantities of toxins and waste products to diffuse into the dialysate via the peritoneal membrane. In particular, the albumin preferably is provided at a concentration sufficient to bind to water insoluble or poorly water soluble toxins or waste products and thus facilitate their removal from the body via the bladder. Other components of the dialysate may include sodium bicarbonate, although sodium chloride or sodium lactate may also suitably be used, and glucose.

Preferably, implantable device 20 is configured to move peritoneal dialysis fluid from the peritoneum to the bladder in quantities and intervals selected to provide sufficient time for a sufficient amount of waste products and toxins to diffuse into the dialysis fluid to maintain or improve the health of the patient's liver and other organs. For example, relatively large quantities (e.g., 1-2.5 liters) may be moved in relatively long intervals (e.g., every 4-8 hours). In other embodiments, implantable device 20 may be configured to move fluid from the peritoneum to the bladder in short (e.g., 10 second) intervals (e.g., every 10-20 minutes). Such short but frequent intervals are expected to inhibit the accumulation of material on the interior lumens of catheters 23 and 25, and reducing the risk for tissue ingrowth. The fluid circuit of implantable device 20 may be configured to provide an average flow rate of about 1-2.5 liters/hour, although much higher and lower flow rates are possible if needed. As described in detail below, the pumping time and volume, including maximum and minimum limits for daily pumped volume and the time the dialysate is allowed to remain in the peritoneal cavity, may be programmed by the physician using monitoring and control system 40 as required for a specific patient.

Additionally, as further described below, implantable device 20 includes pressure sensors that monitor pressure in both the peritoneal cavity and the bladder, such that pumping of fluid into the bladder is disabled until the bladder is determined to have sufficient space to accommodate additional fluid. For patient comfort, implantable device 10 optionally may be programmed not to pump at night or when an accelerometer included in the implantable device indicates that the patient is asleep (and thus unlikely to be able to void the bladder). Implantable device 20 preferably includes multiple separate fail-safe mechanisms, to ensure that urine cannot pass from the bladder to the peritoneal cavity through the pump, thereby reducing the risk of transmitting infection.

Still referring to FIG. 1A, external charging and communication system 30 in a preferred form comprises base 31 and handpiece 32. In this embodiment, handpiece 32 contains a controller, a radio transceiver, an inductive charging circuit, a battery, a quality-of-charging indicator and a display, and is removably coupled to base 31 to recharge its battery. Base 31 may contain a transformer and circuitry for converting conventional 120V power service to a suitable DC current to charge handpiece 32 when coupled to base 31. In alternative embodiments, handpiece 32 may include such circuitry and a detachable power cord, thereby permitting the handpiece to be directly plugged into a convention 120V wall socket to charge the battery. In a preferred embodiment, each of implantable device 20 and handpiece 32 includes a device identifier stored in memory, such that handpiece 32 provided to the patient is coded to operate only with that patient's specific implantable device 20.

Handpiece 32 preferably includes housing 33 having multi-function button 34, display 35, a plurality of light emitting diodes (LEDs, not shown) and inductive coil portion 36. Multi-function button 34 provides the patient the ability to issue a limited number of commands to implantable device 20, while display 35 provides visible confirmation that a desired command has been input; it also displays battery status. Inductive coil portion 36 houses an inductive coil that is used transfer energy from handpiece 32 to recharge the battery of implantable device 20. The LEDs, which are visible through the material of housing 33 when lit, may be arranged in three rows of two LEDs each, and are coupled to the control circuitry and inductive charging circuit contained within handpiece 32. As described in further detail below, the LEDs may be arranged to light up to reflect the degree of inductive coupling achieved between handpiece 32 and implantable device 20 during recharging of the latter. Alternatively, the LEDs may be omitted and an analog display provided on display 35 indicating the quality of inductive coupling.

As further described in detail below, the control circuitry contained within handpiece 32 is coupled to the inductive charging circuit, battery, LEDs and radio transceiver, and includes memory for storing information from implantable device 20. Handpiece 32 also preferably includes a data port, such as a USB port, that permits the handpiece to be coupled to monitoring and control system 40 during visits by the patient to the physician's office. Alternatively, handpiece 32 may include a wireless chip, e.g., conforming to the Bluetooth or IEEE 802.11 wireless standards, thereby enabling the handpiece to communicate wirelessly with monitoring and control system 40, either directly or via the Internet.

Monitoring and control system 40 is intended primarily for use by the physician and comprises software configured to run on a conventional computer, e.g., a laptop as illustrated in FIG. 1A. The software enables the physician to configure, monitor and control operation of charging and communication system 30 and implantable device 20. As described in detail below, the software may include routines for configuring and controlling pump operation, such as a target amount of fluid to move daily or per motor actuation, intervals between pump actuation, and limits on peritoneal cavity pressure, bladder pressure, pump pressure, and battery temperature. System 40 also may provide instructions to implantable device 20 via charging and control system 30 to control operation of implantable device 20 so as not to move fluid during specific periods (e.g., at night) or to defer pump actuation if the patient is asleep. System 40 further may be configured, for example, to send immediate commands to the implantable device to start or stop the pump, or to operate the pump in reverse or at high power to unblock the pump or associated catheters. The software of system 40 also may be configured to download real-time data relating to pump operation, as well as event logs stored during operation of implantable device 20. Based on the downloaded data, e.g., based on measurements made of the patient's temperature, respiratory rate, and/or fluid viscosity, the software of system 40 optionally may be configured to alert the physician to a prediction or detection of infection and/or a change in the patient's health for which an adjustment to the flow rate, volume, time and/or frequency of pump operation may be required. Finally, system 40 optionally may be configured to remotely receive raw or filtered operational data from a patient's handpiece 32 over a secure Internet channel.

Turning now to FIGS. 1B-1E, plan views of various possible configurations of implantable device 20 and dialysate reservoir 45, as implanted in a patient suffering from chronic liver failure, will now be described. Methods of using system 10, including device 20 and dialysate reservoir 45 implanted as illustrated in FIGS. 1B-1E, to treat a patient suffering from chronic liver failure will be provided further below with reference to FIG. 1F.

Figure 1B:
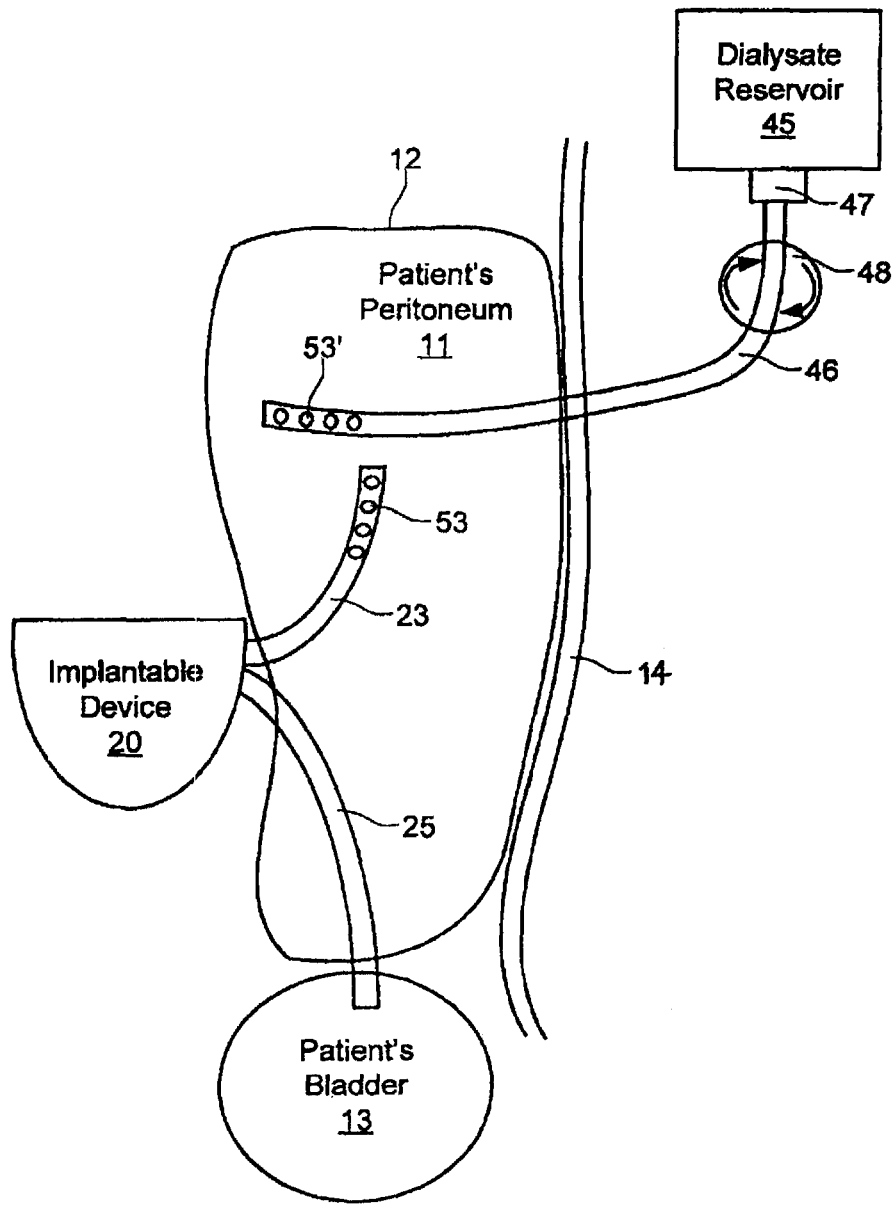
FIG. 1B is a plan view of selected components of the artificial liver system of FIG. 1A as implanted in a patient.

Specifically, FIG. 1B illustrates an embodiment in which implantable device 20 is implanted subcutaneously, preferably outside of the patient's peritoneum 11 as defined by peritoneal membrane 12 but beneath the subject's skin 14 so that it may readily be charged by, and communicate with, charging and communication system 30 illustrated in FIG. 1A. Device 20 is coupled via appropriate connectors (not shown) to peritoneal catheter 23 and bladder catheter 25. Peritoneal catheter 23 is configured for implantation in the patient's peritoneum 11 and preferably includes apertures 53 such as described in further detail below with reference to FIGS. 2A-2B. Bladder catheter 25 is configured for implantation in the patient's bladder 13 and preferably includes an anchor to secure the outlet end of the catheter within the bladder 13, such as described in further detail below with reference to FIGS. 3A-3B.

As illustrated in FIG. 1B, dialysate reservoir 45 is positioned outside of the body and fluidically coupled to the peritoneal cavity via catheter 46. Catheter 46 is coupled to reservoir 45 via connector 47, which is configured so as to allow the patient to periodically replace reservoir 45 with ease. Catheter 46 preferably includes apertures 53', which may be similar in dimension and density to apertures 53, and which allow dialysate to flow into the peritoneum 11 in a relatively diffuse manner. In the illustrated embodiment, external pump 48 is configured to cause dialysate to flow from reservoir 45 into the peritoneum 11 at a desired rate. For example, reservoir 45 may be positioned on belt 57 which is described further below with respect to FIG. 1D and which includes pump 48. Pump 48 may be configured to communicate wirelessly with implantable device 20 so as to coordinate delivery of dialysate into the patient's peritoneum. In an alternative embodiment, dialysate reservoir 45 is positioned at a level above the peritoneum 11 such that gravity causes dialysate to flow from reservoir 45 into the peritoneum at a desired rate. In either embodiment, reservoir 45 preferably provides fluid to the peritoneum 11 in a volume, at a rate, and with a frequency suitable to sufficiently fill the peritoneum with dialysate to allow a sufficient amount of toxins and waste products to diffuse into the dialysate to maintain or improve the health of the patient's liver and/or other organs. Such volume, rate, and frequency may be approximately the same as the volume, rate, and frequency with which implantable device 20 removes used dialysate (with toxins and waste products therein) from the peritoneal cavity to the patient's bladder 13.

Figure 1C:
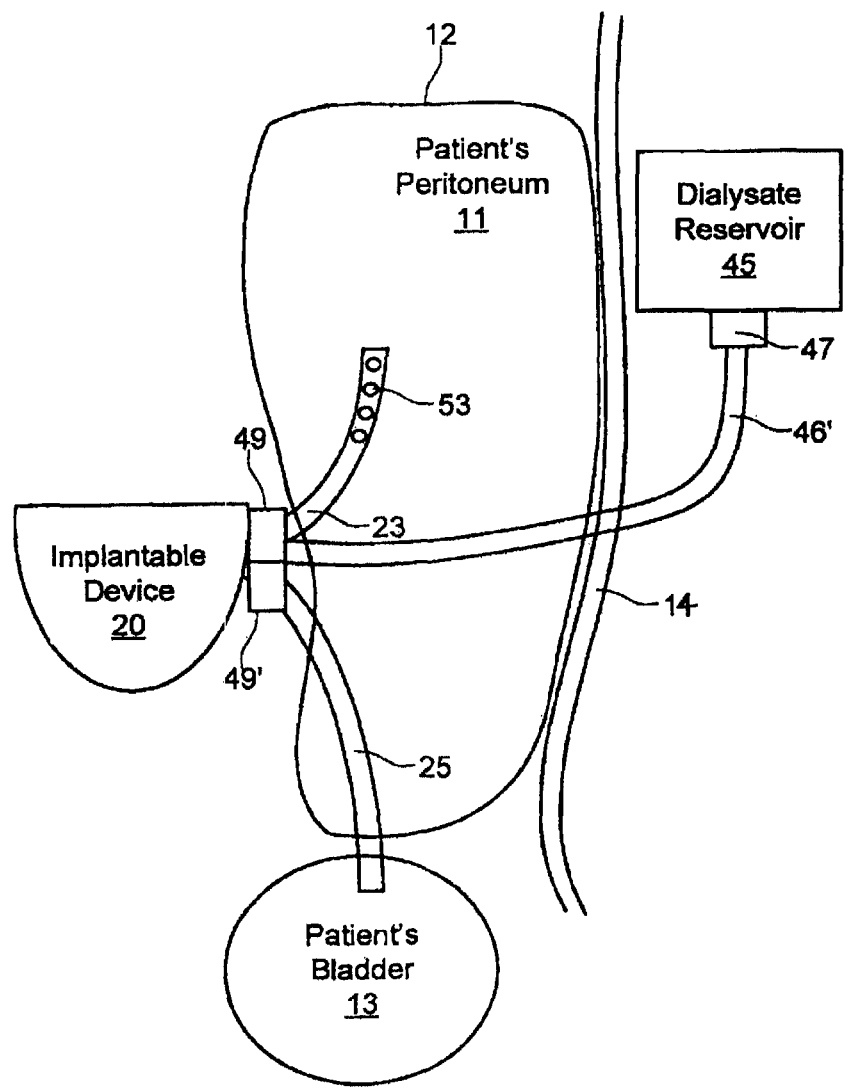
FIG. 1C is a plan view of selected components of an alternative artificial liver system as implanted in a patient.

Alternatively, as illustrated in FIG. 1C, dialysate reservoir 45 may be positioned outside of the patient's body, e.g., using belt 57 described further below with reference to FIG. 1D, and may be coupled to implantable device 20 via catheter 46' and connector 47. Implantable device 20 is configured to pump dialysate into peritoneum 11 from reservoir 45 via catheters 46' and 23, and then at a later time to pump the dialysate from peritoneum 11 into bladder 13 via catheters 23 and 25. Specifically, the inlet 22 of implantable device 20 comprises a first valve 49 to which catheters 23 and 46' are both connected, and the outlet 24 of implantable device 20 comprises a second valve 49' to which catheter 25 is connected. During pumping operations, implantable device 20 controls valves 49 and 49' so as to prevent fluid from being inadvertently pumped from the bladder into the peritoneal cavity. For example, to pump fluid into the peritoneum 11 from reservoir 45, implantable device 20 may close off fluidic communication to catheter 25 by appropriately actuating valve 49', may open fluidic communication between catheters 46' and 23 by appropriately actuating valve 49, and may turn in a first direction so as to pump fluid from reservoir 45 via catheters 46' and 23. Then, after the fluid has been in the peritoneum for a predetermined amount of time, implantable device 20 may pump that fluid to the patient's bladder 13 by closing off fluidic communication to catheter 46' and opening fluidic communication to catheter 23 by appropriately actuating valve 49, opening fluidic communication to catheter 25 by appropriately actuating valve 49', and turning in a second direction (opposite from the first) so as to pump the fluid into bladder 13 via catheters 23 and 25. It should be appreciated that the functionalities of valves 49 and 49' may be provided by any desired number of valves that are disposed appropriately along catheters 23, 25, and 46' and are controllably actuated by implantable device 20, e.g., via valve controller 86 illustrated in FIG. 4. In certain configurations, the use of one or more passive valves (not controlled by implantable device 20) may be appropriate, e.g., valve 49' may be a passive check valve disposed along catheter 25 that inhibits fluid to flow from the bladder to device 20.

Figure 1D:
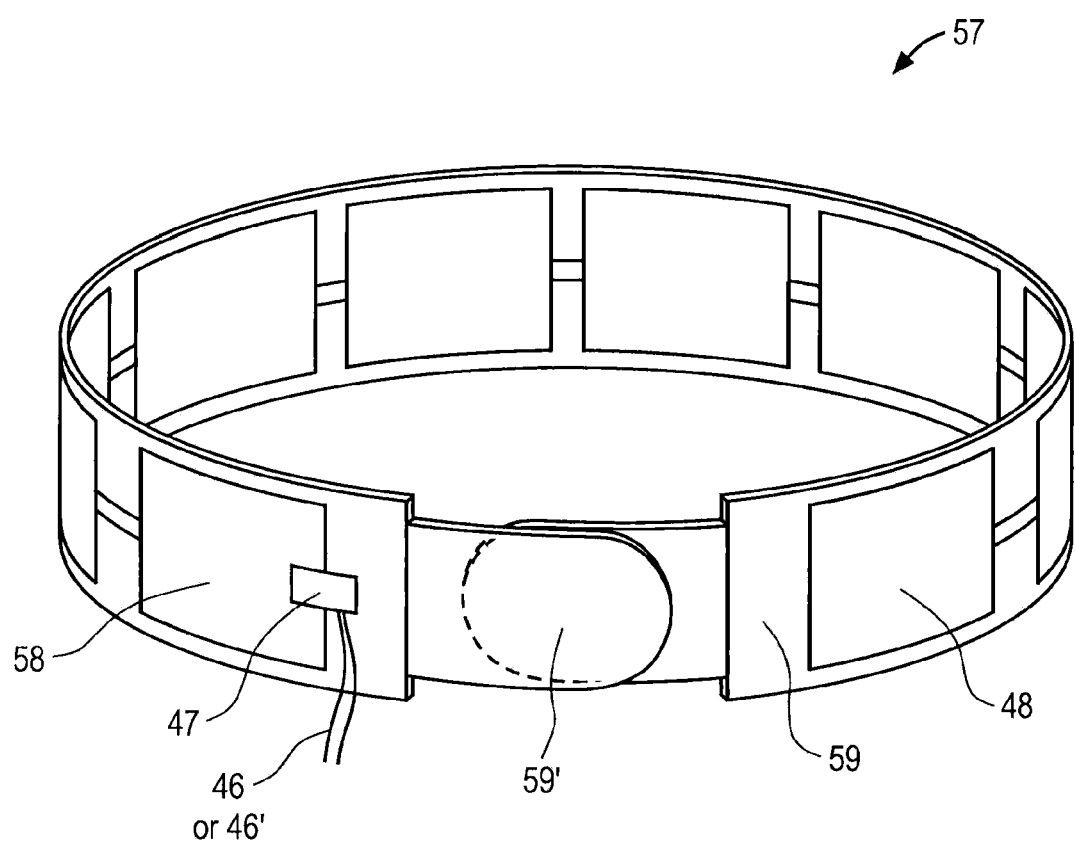
FIG. 1D is a perspective view of a dialysate belt that may be used with the artificial liver systems of FIG. 1B or 1C.

FIG. 1D illustrates a belt 57 that may be used to removably secure reservoir 45 illustrated in FIGS. 1B and 1C to the patient's body. Belt 57 includes pouch(es) 58, flexible band of material 59, fastener 59', and optional pump 48. Pouch(es) 58 may include one long, continuous pouch that contains the peritoneal dialysis fluid, or alternatively may include a plurality of pouches interconnected by catheters, and may be coupled to catheter 46 or 46' via connector 47. Preferably, pouch(es) 58 hold a sufficient amount of dialysate for one day or one treatment cycle, e.g., 1-2.5 liters, and may be configured for single use and easy replaceability, or may be sterilizable and refillable. Pouch(es) 58 may be arranged generally linearly along the length of the flexible band of material 59, and may be secured thereto by an appropriate mechanism, e.g., with thin bands of material secured by snaps, buttons, hook-and-pile fasteners, and the like. Flexible band of material 59 may be formed of any suitable fabric, including but not limited to a stretchable, form-fitting material that may fit unobtrusively under the patient's clothes. Fastener 59' is configured to allow the patient to repeatedly wear belt 57, and may include, for example, snap(s), a buckle, a zipper, or a hook-and-pile fastener, as is illustrated.

Optional pump 48 (including a power source such as a battery, not shown) is configured to facilitate flow of the dialysate into the peritoneum, e.g., as described above with respect to FIG. 1B. Pump 48 may include a wireless transceiver that communicates with implantable device 20 to coordinate delivery of fresh dialysate from the reservoir to the peritoneum with the removal of used dialysate from the peritoneum to the bladder. Additionally, or alternatively, an ultraviolet (UV) source such as described below with respect to FIGS. 4 and 5B, and appropriate power source, may be provided on belt 57 and configured to irradiate the fluid before it enters, or as it enters, catheter 46 or 46'.

Figure 1E:
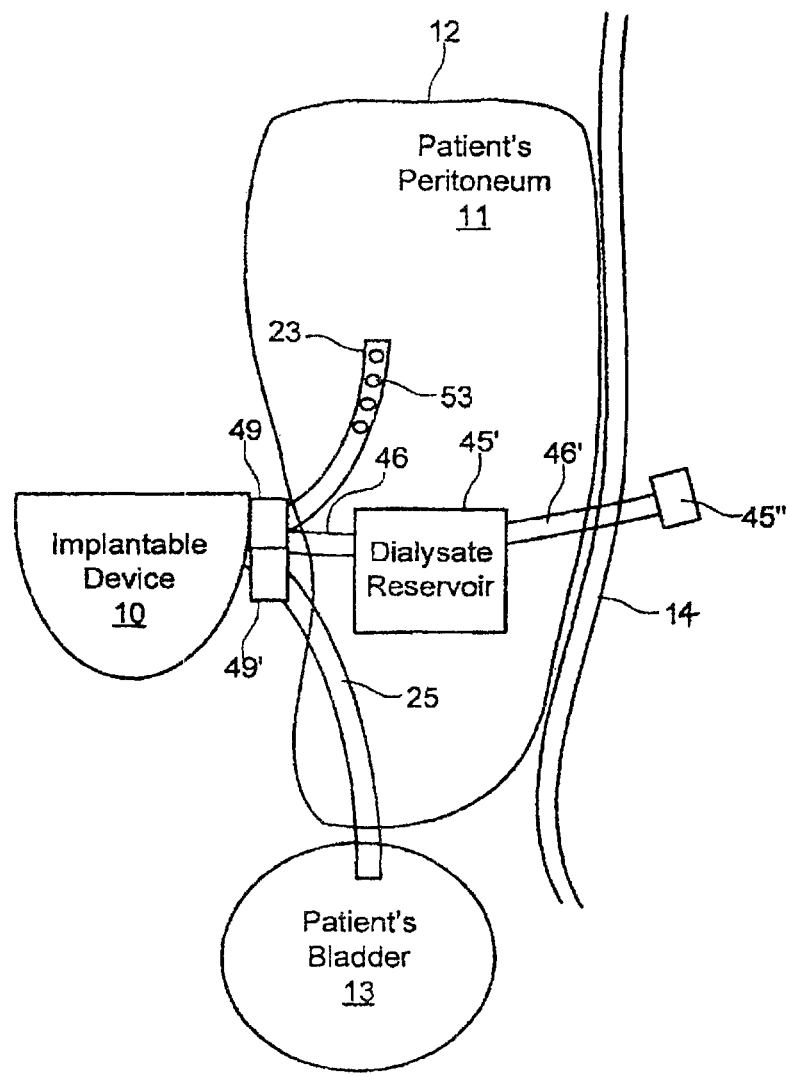
FIG. 1E is a plan view of selected components of another alternative artificial liver system as implanted in a patient.

FIG. 1E illustrates an alternative configuration to those of FIGS. 1B-1D, in which dialysate reservoir 45' is instead implanted within the patient's body, e.g., within the peritoneum 11. Implantable device 20 is configured to pump dialysate into peritoneum 11 from reservoir 45, and then at a later time to pump the dialysate from peritoneum 11 into bladder 13, using catheters 46, 23, and 25 and valves 49 and 49' in a manner analogous to that described above with respect to FIG. 1D. However, instead of positioning dialysate reservoir 45 on belt 47, as illustrated in FIG. 1D, or hanging reservoir 45 over the level of the peritoneum as described above with reference to FIG. 1B, the embodiment illustrated in FIG. 1E may further improve convenience the patient by disposing dialysate reservoir 45' within the peritoneal cavity and providing port 45" and port catheter 46' via which the patient may periodically fill the reservoir. In one illustrative embodiment, port 45" comprises a flexible, self-sealing membrane that the patient may pierce with a needle connected to a separate, external reservoir (not shown) that contains fresh dialysate for re-filling internal reservoir 45'.

Figure 1F:
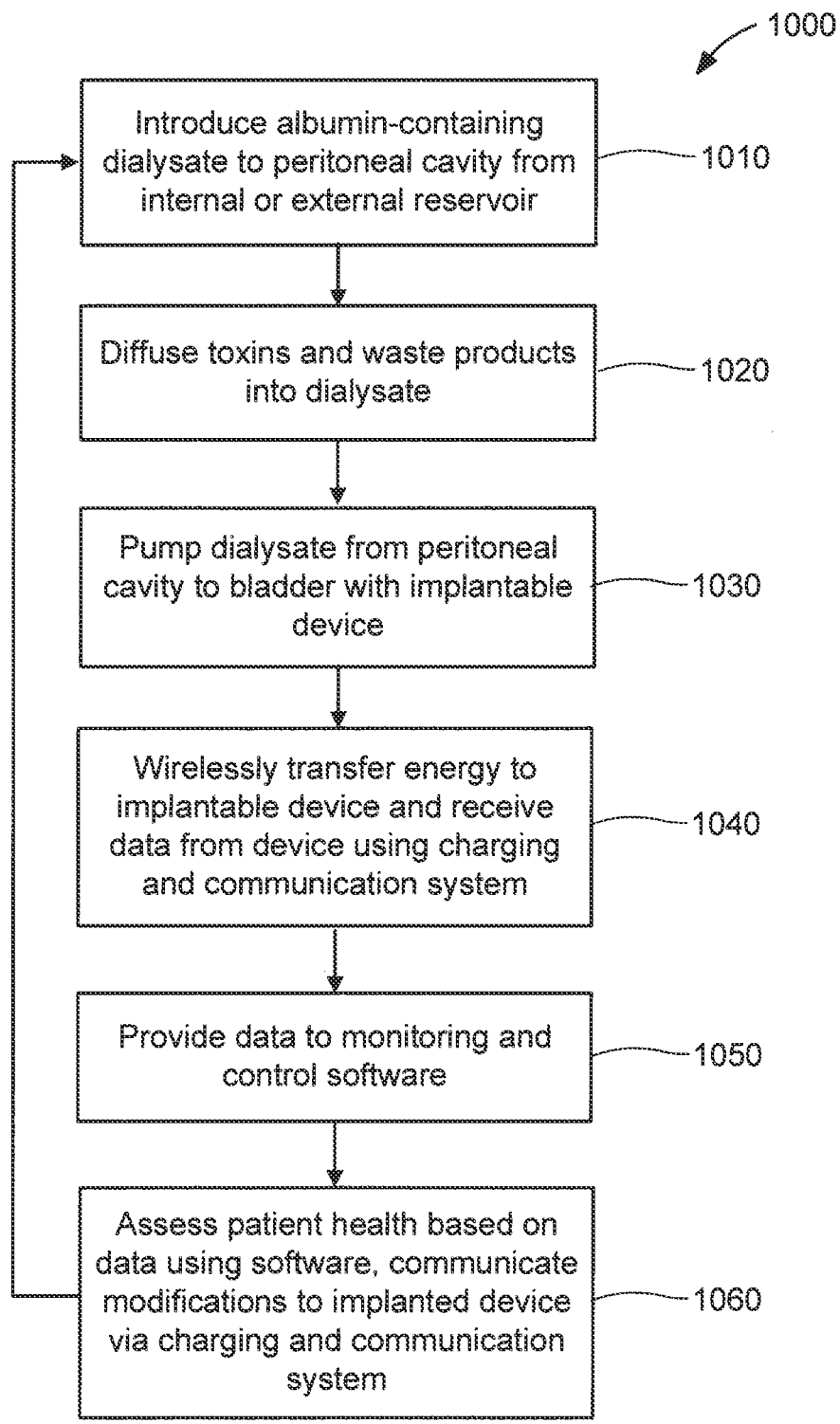
FIG. 1F illustrates steps in an exemplary method of using the artificial liver systems of FIGS. 1A-1E.

Methods of using artificial liver systems such as illustrated in FIGS. 1A-1E will now be described with reference to FIG. 1F.

Method 1000 illustrated in FIG. IF includes introducing albumin-containing dialysate to the peritoneal cavity from a reservoir that is internal or external to the patient's body (step 1010). For example, as described above with reference to FIGS. 1B and 1D, the dialysate may be introduced using an external pump or gravity. Or, as described above with reference to FIGS. 1C and 1E, the dialysate may be introduced using implantable device 20 and one or more valves in communication therewith. A sufficient amount of dialysate is introduced to allow a sufficient amount of toxins and waste products to be removed when that dialysate is removed from the peritoneum.

Toxins and waste products then diffuse into the dialysate, e.g., via the peritoneal membrane, thus reducing the levels of those toxins and waste products in the patient's blood (step 1020). In particular, it is believed that the albumin in the dialysate will bind to water-insoluble and poorly water soluble toxins and waste products, thus enhancing transport of such toxins and waste products out of the body relative to a dialysate that lacks albumin.

Dialysate then is pumped from the peritoneal cavity to the bladder with the implantable device (step 1030). Such pumping may occur after the dialysate has been in the peritoneum for a sufficient amount of time to draw a sufficient amount of toxins and waste products out of the body to maintain, or even improve, the health of the liver and/or other organs.

Energy may be wirelessly transferred to the implantable device, and data received from the device, using a charging and communication system such as described briefly above with reference to FIG. 1A and as described in greater detail below with reference to FIGS. 8A-9 (step 1040). For example, the implantable device may record parameters reflective of the health of the patient and the operation of the device, which parameters may be communicated to the charging and communication system.

The data, e.g., parameters recorded by the implantable device, then is provided to monitoring and control software, which is in communication with the charging and communication system and is under the control of the treating physician (step 1050).

Based on those parameters, the health of the patient may be assessed using the software, and the physician may remotely communicate any modifications to the flow rate, volume, time duration, or frequency with which the implantable device is to maintain the dialysate in the peritoneal cavity before removing it to the bladder (step 1060). Such communication may be performed via the charging and communication system.

Further details of selected components of the artificial liver systems and methods of FIGS. 1A-1F will now be provided with reference to FIGS. 2A-15.

Peritoneal and Bladder Catheters

Figure 2A:
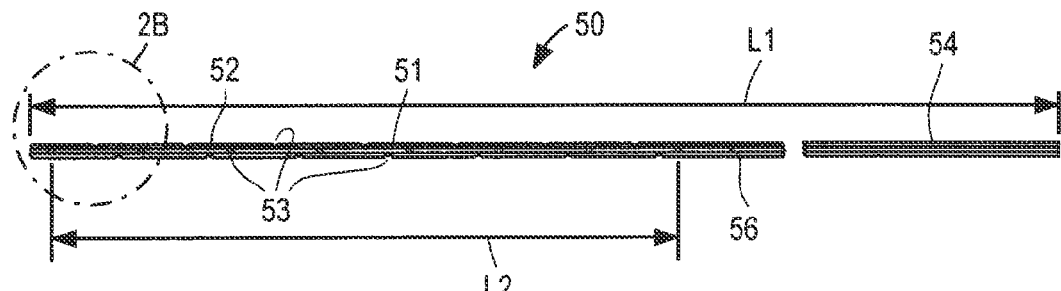
FIGS. 2A and 2B are, respectively, side view and perspective detailed views of an exemplary embodiment of a peritoneal catheter suitable for use with the artificial liver system of the present invention, in which FIG. 2B corresponds to detail region 2B of FIG. 2A.
Figure 2B:
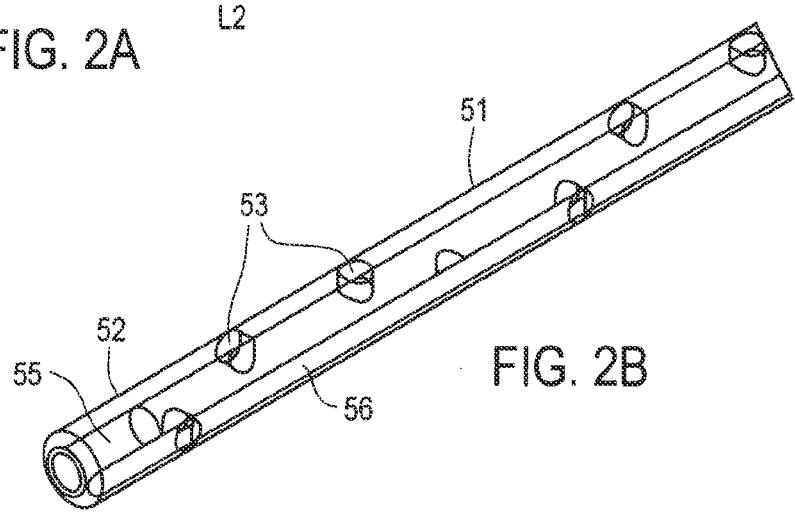

Referring to FIGS. 2A and 2B, exemplary peritoneal catheter 50 constructed in accordance with the principles of the present invention is described. Peritoneal catheter 50 corresponds to peritoneal catheter 23 described above with reference to FIGS. 1A-1E, and preferably comprises tube 51 of medical-grade silicone including inlet (distal) end 52 having a plurality of through-wall holes 53 and outlet (proximal) end 54. Peritoneal catheter preferably has length L1 of about 40 cm, with holes 53 extending over length L2 of about 24 cm from inlet end 52. Holes 53 preferably are arranged circumferentially offset by about 90° and longitudinally offset between about 8 mm to 10 mm, as shown in FIG. 2B. In one preferred embodiment, 29 holes 53 are arranged in four rows of 7 holes each, extend only through one wall of the peritoneal catheter at each location, and have a size of between 2.0 to 2.5 mm. Peritoneal catheter 50 preferably includes solid silicone plug 55 that fills distal end of the lumen for a distance of about 7-10 mm to reduce tissue ingrowth, and radiopaque strip 56 disposed on, or embedded within, the catheter that extends the entire length of the catheter, that renders the catheter visible in fluoroscopic or X-ray images. Peritoneal catheter 50 may also include a polyester cuff (not shown) in the region away from holes 53, to promote adhesion of the catheter to the surrounding tissue, thereby anchoring it in place.

Alternatively, inlet end 52 of peritoneal catheter 50 may have a spiral configuration, and an atraumatic tip, with holes 53 distributed over a length of the tubing to reduce the risk of clogging. As a further alternative, inlet end 52 may include a portion having an enlarged diameter, as disclosed in U.S. Pat. No. 4,657,530, or a reservoir as disclosed in FIGS. 9 to 16 of U.S. Patent Application Publication US 2009/0318844, the entire contents of both of which are incorporated herein by reference, to further reduce the risk of clogging. Inlet end 52 also may terminate in a duck-bill valve, as shown for example in U.S. Pat. No. 4,240,434, thereby permitting the catheter to be cleaned in situ by disconnecting the outlet end of the catheter from implantable device 20 and extending a rod from the outlet end of catheter 50 through the duckbill valve at the inlet end.

Inlet end 52 also may include a polyester cuff to promote adhesion of the catheter to an adjacent tissue wall, thereby ensuring that the inlet end of the catheter remains in position. Outlet end 54 also may include a connector for securing the outlet end of the peritoneal catheter to implantable device 20. In one preferred embodiment, the distal end of the peritoneal catheter, up to the ingrowth cuff, may be configured to pass through a conventional 16 F peel-away sheath. In addition, the length of the peritoneal catheter may be selected to ensure that it lays along the bottom of the body cavity, and is sufficiently resistant to torsional motion so as not to become twisted or kinked during or after implantation.

Figure 3A:
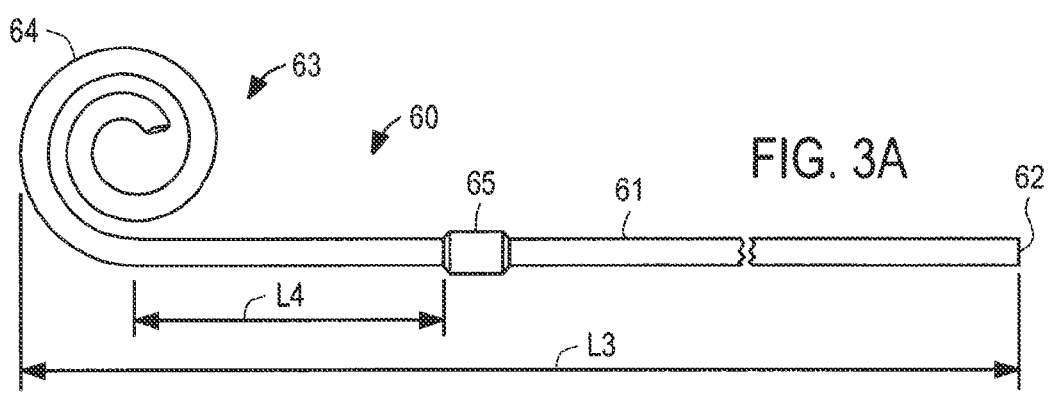
FIGS. 3A and 3B are, respectively, side and perspective views, respectively, of first and second embodiments of bladder catheters suitable for use with the artificial liver system of the present invention.

With respect to FIG. 3A, a first embodiment of bladder catheter 60 of the present invention is described, corresponding to bladder catheter 25 of FIGS. 1A-1E. Bladder catheter 60 preferably comprises tube 61 of medical-grade silicone having inlet (proximal) end 62 and outlet (distal) end 63 including spiral structure 64, and polyester ingrowth cuff 65. Bladder catheter 60 includes a single internal lumen that extends from inlet end 62 to a single outlet at the tip of spiral structure 64, commonly referred to as a "pigtail" design. Inlet end 62 may include a connector for securing the inlet end of the bladder catheter to implantable device 20, or may have a length that can be trimmed to fit a particular patient. In one example, bladder catheter 60 may have length L3 of about 45 cm, with cuff 65 placed length L4 of about 5 to 6 cm from spiral structure 64. Bladder catheter 60 may be loaded onto a stylet with spiral structure 64 straightened, and implanted using a minimally invasive technique in which outlet end 63 and spiral structure 64 are passed through the wall of a patient's bladder using the stylet. When the stylet is removed, spiral structure 64 returns to the coiled shape shown in FIG. 3A. Once outlet end 63 of bladder catheter 60 is disposed within the patient's bladder, the remainder of the catheter is implanted using a tunneling technique, such that inlet end 62 of the catheter may be coupled to implantable device 20. Spiral structure 64 may reduce the risk that outlet end 63 accidentally will be pulled out of the bladder before the tissue surrounding the bladder heals sufficiently to incorporate ingrowth cuff 65, thereby anchoring the bladder catheter in place.

In a preferred embodiment, bladder catheter 60 is configured to pass through a conventional peel-away sheath. Bladder catheter 60 preferably is sufficiently resistant to torsional motion so as not to become twisted or kinked during or after implantation. In a preferred embodiment, peritoneal catheter 50 and bladder catheter 60 preferably are different colors, have different exterior shapes (e.g., square and round) or have different connection characteristics so that they cannot be inadvertently interchanged during connection to implantable device 20. Optionally, bladder catheter 60 may include an internal duckbill valve positioned midway between inlet 62 and outlet end 63 of the catheter to ensure that urine does not flow from the bladder into the peritoneal cavity if the bladder catheter is accidentally pulled free from the pump outlet of implantable device 20 and/or if the pump of implantable device 20 is actuated so as to draw peritoneal dialysate fluid from reservoir 45 into the patient's peritoneal cavity.

In an alternative embodiment, the peritoneal and bladder catheters devices may incorporate one or several anti-infective agents to inhibit the spread of infection between body cavities. Examples of anti-infective agents which may be utilized may include, e.g., bacteriostatic materials, bacteriocidal materials, one or more antibiotic dispensers, antibiotic eluting materials, and coatings that prevent bacterial adhesion, and combinations thereof. Additionally, implantable device 20 may include a UV lamp configured to irradiate fluid in the peritoneal and/or bladder catheters so as to kill any pathogens that may be present and thus inhibit the development of infection, as described further below with respect to FIGS. 4 and 5B.

Alternatively, rather than comprising separate catheters, peritoneal and bladder catheters 50, 60 may share a common wall, which may be convenient because the bladder and peritoneal cavity share a common wall, thereby facilitating insertion of a single dual-lumen tube. In addition, either or both of the peritoneal or bladder catheters may be reinforced along a portion of its length or along its entire length using ribbon or wire braiding or lengths of wire or ribbon embedded or integrated within or along the catheters. The braiding or wire may be fabricated from metals such as stainless steels, superelastic metals such as nitinol, or from a variety of suitable polymers. Such reinforcement may also be used for catheter 46 connected to reservoir 45.

Figure 3B:
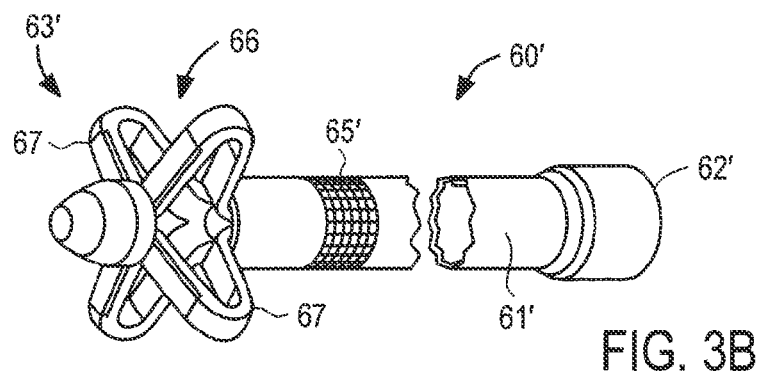

With respect to FIG. 3B, a second embodiment of an bladder catheter of the present invention is described, in which similar components are identified with like-primed numbers. Bladder catheter 60' preferably comprises tube 61' of medical-grade silicone having inlet end 62', outlet end 63' and polyester ingrowth cuff 65'. In accordance with this embodiment, outlet end 63' includes malecot structure 66, illustratively comprising four resilient wings 67 that expand laterally away from the axis of the catheter to reduce the risk that outlet end 63' of the catheter will be inadvertently pulled loose after placement. Inlet end 62' may include a connector for securing the inlet end of the bladder catheter to implantable device 20, or may have a length that can be trimmed to fit a particular patient.

Malecot structure 66 preferably is constructed so that wings 67 deform to a substantially flattened configuration when a stylet is inserted through the lumen of the catheter. In this manner, bladder catheter 60' may be loaded onto a stylet, and using a minimally invasive technique, outlet end 63' and malecot structure 66 may be passed through the wall of a patient's bladder using the stylet. When the stylet is removed, wings 67 of the malecot structure return to the expanded shape shown in FIG. 3B. Once outlet end 63' of bladder catheter 60' is coupled to the patient's bladder, the remainder of the catheter is implanted using a tunneling technique, such that inlet end 62' of the catheter may be coupled to implantable device 20. Malecot structure 66 may reduce the risk that outlet end 63' accidentally will be pulled out of the bladder before the tissue surrounding the bladder heals sufficiently to incorporate ingrowth cuff 65'. As for the embodiment of FIG. 3A, the bladder catheter of FIG. 3B may be configured to pass through a conventional peel-away sheath, and preferably is sufficiently resistant to torsional motion so as not to become twisted or kinked during or after implantation.

The Implantable Device

Referring now to FIG. 4, a schematic depicting the functional blocks of implantable device 20 of the present invention is described. Implantable device 20 includes control circuitry, illustratively processor 70 coupled to nonvolatile memory 71, such as flash memory or electrically erasable programmable read only memory, and volatile memory 72 via data buses. Processor 70 is electrically coupled to electric motor 73, battery 74, inductive circuit 75, radio transceiver 76, UV lamp 85, and a plurality of sensors, including humidity sensor 77, a plurality of temperature sensors 78, accelerometer 79, a plurality of pressure sensors 80, and respiratory rate sensor 81. Inductive circuit 75 is electrically coupled to coil 84 to receive energy transmitted from charging and communication system 30, while transceiver 76 is coupled to antenna 82, and likewise is configured to communicate with a transceiver in charging and communication system 30, as described below. Optionally, inductive circuit 75 also may be coupled to infrared light emitting diode 83. Motor 73 may include a dedicated controller, which interprets and actuates motor 73 responsive to commands from processor 70. Optionally, processor 70 is further in communication with valve controller 86. All of the components depicted in FIG. 4 are contained within a low volume sealed biocompatible housing, as shown in FIG. 5A.

Processor 70 executes firmware stored in nonvolatile memory 71 which controls operation of motor 73 responsive to signals generated by motor 73, sensors 77-81 and commands received from transceiver 76. Processor 70 also controls reception and transmission of messages via transceiver 76 and operation of inductive circuit 75 to charge battery 74. In addition, processor 70 receives signals generated by Hall Effect sensors located within motor 73, which are used to compute direction and revolutions of the gears of the gear pump, and thus fluid volume pumped and the viscosity of that fluid, as described below. Processor 70 preferably includes a low-power mode of operation and includes an internal clock, such that the processor can be periodically awakened to handle pumping, pump tick mode, or communications and charging functions, and/or awakened to handle commands received by transceiver 76 from handpiece 32. In one embodiment, processor 70 comprises a member of the MSP430 family of microcontroller units available from Texas Instruments, Incorporated, Dallas, Tex., and may incorporate the nonvolatile memory, volatile memory, and radio transceiver components depicted in FIG. 4. In addition, the firmware executed on processor 70 may be configured to respond directly to commands sent to implantable device 20 via charging and communication system 30. Processor 70 also is configured to monitor operation of motor 72 (and any associated motor controller) and sensors 77-81, as described below, and to store data reflecting operation of the implantable device, including event logs and alarms. Thus, data is reported to the charging and communication system when it is next wirelessly coupled to the implantable device. In a preferred embodiment, processor 70 generates up to eighty log entries per second prior to activating the pump, about eight log entries per second when the implantable system is actively pumping and about one log entry per hour when not pumping.

Nonvolatile memory 71 preferably comprises flash memory or EEPROM, and stores a unique device identifier for implantable device 20, firmware to be executed on processor 70, configuration set point data relating to operation of the implantable device, and optionally, coding to be executed on transceiver 76 and/or inductive circuit 75, and a separate motor controller, if present. Firmware and set point data stored on nonvolatile memory 71 may be updated using new instructions provided by control and monitoring system 40 via charging and communication system 30. Volatile memory 72 is coupled to and supports operation of processor 70, and stores data and event log information gathered during operation of implantable device 20. Volatile memory 72 also serves as a buffer for communications sent to, and received from, charging and communication system 30.

Transceiver 76 preferably comprises a radio frequency transceiver and is configured for bi-directional communications via antenna 76 with a similar transceiver circuit disposed in handpiece 32 of charging and communication system 30. Transceiver 76 also may include a low power mode of operation, such that it periodically awakens to listen for incoming messages and responds only to those messages including the unique device identifier assigned to that implantable device. Alternatively, because transceiver 76 communicates only with the corresponding transceiver in handpiece 32 of its associated charging and communication system 30, transceiver 76 may be configured to send or receive data only when inductive circuit 75 of the implantable device is active. In addition, transceiver 76 may employ an encryption routine to ensure that messages sent from, or received by, the implantable device cannot be intercepted or forged.

Inductive circuit 75 is coupled to coil 84, and is configured to recharge battery 74 of the implantable device when exposed to a magnetic field supplied by a corresponding inductive circuit within handpiece 32 of charging and communication system 30. In one embodiment, inductive circuit 75 is coupled to optional infrared LED 83 that emits an infrared signal when inductive circuit 75 is active. The infrared signal may be received by handpiece 32 of charging and communication system 30 to assist in locating the handpiece relative to the implantable device, thereby improving the magnetic coupling and energy transmission to the implantable device.

In accordance with one aspect of the present invention, inductive circuit 75 optionally may be configured not only to recharge battery 74, but to directly provide energy to motor 73 in a "boost" mode or jog/shake mode to unblock the pump. In particular, if processor 70 detects that motor 73 is stalled, e.g., due to a block created by proteins in the peritoneal dialysis fluid, an alarm may be stored in memory. When implantable device 20 next communicates with charging and communication system 30, the alarm is reported to handpiece 32, and the patient may be given the option of depressing multifunction button 34 to apply an overvoltage to motor 73 from inductive circuit 75 for a predetermined time period to free the pump blockage. Alternatively, depressing the multi-function button may cause processor 70 to execute a set of commands by which motor 73 is jogged or shaken, e.g., by alternatingly running the motor is reverse and then forward, to disrupt the blockage. Because such modes of operation may employ higher energy consumption than expected during normal operation, it is advantageous to drive the motor during such procedures with energy supplied via inductive circuit 75.

Battery 74 preferably comprises a lithium ion or lithium polymer battery capable of long lasting operation, e.g., up to three years, when implanted in a human, so as to minimize the need for re-operations to replace implantable device 20. In one preferred embodiment, battery 74 supplies a nominal voltage of 3.6V, a capacity of 150 mAh when new, and a capacity of about 120 mAh after two years of use. Preferably, battery 74 is configured to supply a current of 280 mA to motor 73 when pumping; 25 mA when the transceiver is communicating with charging and communication system 30; 8 mA when processor 70 and related circuitry is active, but not pumping or communicating; and 0.3 mA when the implantable device is in low power mode. More preferably, battery 74 should be sized to permit a minimum current of at least 450 mAh for a period of 10 seconds and 1 A for 25 milliseconds during each charging cycle.

Motor 73 preferably is a brushless direct current or electronically commuted motor having a splined output shaft that drives a set of floating gears that operate as a gear pump, as described below. Motor 73 may include a dedicated motor controller, separate from processor 70, for controlling operation of the motor. Motor 73 may include a plurality of Hall Effect sensors, preferably two or more, for determining motor position and direction of rotation. Due to the high humidity that may be encountered in implantable device 20, processor 70 may include programming to operate motor 73, although with reduced accuracy, even if some or all of the Hall Effect sensors fail.

In a preferred embodiment, motor 73 is capable of driving the gear pump to generate a nominal flow rate of 150 ml/min and applying a torque of about 1 mNm against a pressure head of 30 cm water at 3000 RPM. In this embodiment, the motor preferably is selected to drive the gears at from 1000 to 5000 RPM, corresponding to flow rates of from 50 to 260 ml/min, respectively. The motor preferably has a stall torque of at least 3 mNm at 500 mA at 3 V, and more preferably 6 mNm in order to crush non-solid ascitic proteinaceous materials. As discussed above, the motor preferably also supports a boost mode of operation, e.g., at 5 V, when powered directly through inductive circuit 75. Motor 73 preferably also is capable of being driven in reverse as part of a jogging or shaking procedure to unblock the gear pump.

In accordance with one aspect of the present invention, processor 70 may be programmed to automatically and periodically wake up and enter a pump tick mode. In this mode of operation, the gear pump is advanced slightly, e.g., about 120° as measured by the Hall Effect sensors, before processor 70 returns to low power mode. Preferably, this interval is about every 20 minutes, although it may be adjusted by the physician using the monitoring and control system. This pump tick mode is expected to prevent the peritoneal dialysis fluid, which may have a high protein content, from partially solidifying, and blocking the gear pump.

In addition, processor 70 also may be programmed to enter a jog or shake mode when operating on battery power alone, to unblock the gear pump. Similar to the boost mode available when charging the implantable device with the handpiece of charging and communication system 30, the jog or shake mode causes the motor to rapidly alternate the gears between forward and reverse directions to crush or loosen and proteinaceous buildup in the gear pump or elsewhere in the fluid path. Specifically, in this mode of operation, if the motor does not start to turn within a certain time period after it is energized (e.g., 1 second), the direction of the motion is reversed for a short period of time and then reversed again to let the motor turn in the desired direction. If the motor does still not turn (e.g., because the gear pump is jammed) the direction is again reversed for a period of time (e.g., another 10 msec). If the motor still is not able to advance the time interval between reversals of the motor direction is reduced to allow for the motor to develop more power, resulting in a shaking motion of the gears. If the motor does not turn forward for more than 4 seconds, the jog mode of operation is stopped, and an alarm is written to the event log. If the motor was unable to turn forward, processor 70 will introduce a backwards tick before the next scheduled fluid movement. A backward tick is the same as a tick (e.g., about 120° forward movement of the motor shaft) but in the reverse direction, and is intended to force the motor backwards before turning forward, which should allow the motor to gain momentum.

Sensors 77-81 continually monitor humidity, temperature, acceleration, pressure, and respiratory rate, and provide corresponding signals to processor 70 which stores the corresponding data in memory 71 for later transmission to monitoring and control system 40. In particular, humidity sensor 77 is arranged to measure humidity within the housing of the implantable device, to ensure that the components of implantable device are operated within expected operational limits. Humidity sensor 77 preferably is capable of sensing and reporting humidity within a range or 20% to 100% with high accuracy. One or more of temperature sensors 78 may be disposed within the housing and monitor the temperature of the implantable device, and in particular battery 74 to ensure that the battery does not overheat during charging, while another one or more of temperature sensors 78 may be disposed so as to contact fluid entering at inlet 62 and thus monitor the temperature of the fluid, e.g., for use in assessing the patient's health. Accelerometer 79 is arranged to measure acceleration of the implant, preferably along at least two axes, to detect periods of inactivity, e.g., to determine whether the patient is sleeping. This information is provided to processor 70 to ensure that the pump is not operated when the patient is indisposed to attend to voiding of the bladder.

Implantable device 20 preferably includes multiple pressure sensors 80, which are continually monitored during waking periods of the processor. As described below with respect to FIG. 6A, the implantable device of the present invention preferably includes four pressure sensors: a sensor to measure the pressure in the peritoneal cavity, a sensor to measure the ambient pressure, a sensor to measure the pressure at the outlet of the gear pump, and a sensor to measure the pressure in the bladder. These sensors preferably are configured to measure absolute pressure between 450 mBar and 1300 mBar while consuming less than 50 mW at 3V. Preferably, the sensors that measure pressure at the pump outlet and in the bladder are placed across a duckbill valve, which prevents reverse flow of urine and/or used dialysate back into the gear pump and also permits computation of flow rate based on the pressure drop across the duckbill valve.

Respiratory rate monitor 81 is configured to measure the patient's respiratory rate, e.g., for use in assessing the patient's health. Alternatively, the patient's respiratory rate may be measured based on the outputs of one or more of pressure sensors 80, e.g., based on changes in the ambient pressure or the pressure in the peritoneal cavity caused by the diaphragm periodically compressing that cavity during breathing.

Note that any desired number of additional sensors for measuring the health of the patient may also be provided in operable communication with processor 70 and may output recordable parameters for storage in memory 71 and transmission to monitoring and control system 40, that the physician may use to assess the patient's health. For example, chemical or biochemical sensors may be provided that are configured to monitor the levels of one or more toxins or waste products in the peritoneal dialysis fluid.

In preferred embodiments, processor 70 is programmed to pump a predetermined volume of fluid from the peritoneal cavity to the bladder after that fluid has been in the peritoneal cavity for a predetermined amount of time and with a predetermined frequency. Such volume, time, and frequency preferably are sufficient for a sufficient amount of toxins and waste products to diffuse into the fluid via the peritoneal membrane to maintain or improve the health of the patient's liver and/or other organs. The volume, time, and frequency may be selected upon the health of the patient's liver, kidneys, and/or other organs, the activity and habits of the patient, the permeability of the peritoneal membrane to the toxins and waste products, and the osmotic characteristics of the dialysate. For example, the physician may initially program processor 70 with a first time, volume, and frequency based on his perception of the patient's health and habits, and later may adjust that initial programming to vary the volume, time, and/or frequency based on his perception of changes in the patient's health, for example based on changes over time in parameters measured by implantable device 20 and relayed to the physician via monitoring and control software 40.

In other embodiments, processor 70 is programmed to pump fluid from the peritoneal cavity to the bladder only when the pressure in the peritoneum exceeds a first predetermined value, and the pressure in the bladder is less than a second predetermined value, so that the bladder does not become overfull. To account for patient travel from a location at sea level to a higher altitude, the ambient pressure measurement may be used to calculate a differential value for the peritoneal pressure. In this way, the predetermined pressure at which the pump begins operation may be reduced, to account for lower atmospheric pressure. Likewise, the ambient pressure may be used to adjust the predetermined value for bladder pressure. In this way, the threshold pressure at which the pumping ceases may be reduced, because the patient may experience bladder discomfort at a lower pressure when at a high altitude location.

Optionally, controller 70 is in operable communication with UV lamp 85, which is configured to irradiate and thus kill pathogens in the peritoneal dialysis fluid both before and after that fluid is provided to the peritoneal cavity. UV lamp 85 preferably generates light in the UV-C spectral range (about 200-280 nm), particularly in the range of about 250-265 nm, which is also referred to as the "germicidal spectrum" because light in that spectral range breaks down nucleic acids in the DNA of microorganisms. Low-pressure mercury lamps have an emission peak at approximately 253.7 nm, and may suitably be used for UV lamp 85. Alternatively, UV lamp 85 may be a UV light emitting diode (LED), which may be based on AlGaAs or GaN.

Under the control of controller 70, UV lamp 85 irradiates any peritoneal dialysis fluid that enters the implantable device for a preselected amount of time sufficient to kill pathogens that may be present in that fluid. Specifically, the flow rate of the fluid through the device may be selected (e.g., pre-programmed) so as to irradiate the fluid with a sufficient dosage of UV light to inhibit the growth of colonies of pathogens. For example, it is known that dosages of 253.7 nm UV light of between about 5,500-7,000 $\mu$Ws/cm$^2$ are sufficient to provide 100% kill rates for many organisms, including *E. coli, Proteus* spp., *Klebsiella* spp., *Serratia* spp., *Leptospirosis* spp., *Staphylococcus haemolyticus*, and *Enterococci*. Higher dosages, e.g., between about 8,500-12,000 $\mu$Ws/cm$^2$, may be required to provide 100% kill rates for other organisms, including *Kliebsiella* ssp., *Enterobacter* spp., *Psuedomonas* spp., and *Neisseria* gonorrhoeae. However, the dosage to sufficiently inhibit colony growth may be lower. For example, *E. coli* requires only 3000 $\mu$Ws/cm$^2$ to inhibit growth, whereas 6,600 $\mu$Ws/cm$^2$ may be needed to provide a 100% kill rate. Controller 70 may be pre-programmed to set a flow rate of fluid through the tubing sufficient to inhibit colony growth of one or more target pathogens based on the intensity of UV lamp 85, the reflective conditions within the portion of the housing in which UV lamp 85 is used (e.g., upper portion 93 described below with reference to FIG. 5B), the configuration of the tubing being exposed to the UV lamp, the distance between the tubing and the UV lamp, and the susceptibility of target pathogens to the spectrum emitted by UV lamp 85.

Still referring to FIG. 4, in some embodiments processor 70 also may be in communication with valve controller 86; alternatively, valve controller 86 may be part of the functionality of processor 70. Valve controller 86 controls the actuation of any valves that may be used to control the flow of peritoneal dialysis fluid between the reservoir, the peritoneum, and the bladder. For example, as described above with reference to FIGS. 1C and 1E, implantable device 20 may be configured to pump peritoneal dialysis fluid from an external or internal reservoir to the peritoneum, while actuating valves 49 and 49' so as to close fluidic access to the bladder and thus avoid inadvertently pumping fluid from the bladder into the peritoneum; and may be configured to pump peritoneal dialysis fluid from the peritoneum to the bladder, while actuating valves 49 and 49' so as to close fluidic access to the reservoir and thus avoid inadvertently pumping fluid from the peritoneum into the reservoir. Valve controller 86 may coordinate the actuation of valves 49 and 49' in such a manner, or in any other appropriate manner based on the particular valve configuration.

Referring now to FIGS. 5A and 5B, further details of an exemplary embodiment of implantable device 90 are provided. In FIG. 5A, housing 91 is shown as transparent, although it should of course be understood that housing 91 comprises opaque biocompatible plastic and/or metal alloy materials. In FIG. 5B, the implantable device is shown with lower portion 92 of housing 91 removed from upper housing 93 and without a glass bead/epoxy filler material that is used to prevent moisture from accumulating in the device. In FIGS. 5A and 5B, motor 94 is coupled to gear pump housing 95, which is described in greater detail with respect to FIGS. 6 and 7. The electronic components discussed above with respect to FIG. 4 are disposed on flexible circuit board substrate 96, which extends around and is fastened to support member 97. Coil 98 (corresponding to coil 84 of FIG. 4) is disposed on flap 99 of the substrate and is coupled to the electronic components on flap 100 by flexible cable portion 101. Support member 97 is fastened to upper housing 93 and provides a cavity that holds battery 102 (corresponding to battery 74 of FIG. 4). Lower portion 92 of housing 91 includes port 103 for injecting the glass bead/epoxy mixture after upper portion 93 and lower portion 92 of housing 91 are fastened together, to reduce space in the housing in which moisture can accumulate.

Housing 91 also may include features designed to reduce movement of the implantable pump once implanted within a patient, such as a suture hole to securely anchor the implantable device to the surrounding tissue. Housing 91 may in addition include a polyester ingrowth patch that facilitates attachment of the implantable device to the surrounding tissue following subcutaneous implantation.

Additionally, the implantable device optionally may incorporate anti-clogging agents, such enzyme eluting materials that specifically target the proteinaceous components of ascites, enzyme eluting materials that specifically target the proteinaceous and encrustation promoting components of urine, chemical eluting surfaces, coatings that prevent adhesion of proteinaceous compounds, and combinations thereof. Such agents, if provided, may be integrated within or coated upon the surfaces of the various components of the system.

As illustrated in FIG. 5B, upper housing 93 optionally includes UV lamp 85 described further above with respect to FIG. 4. Within upper housing 93, the fluid channels 88 for conducting the peritoneal dialysis fluid may extend approximately linearly, or alternatively may include one or more curves or bends so as to increase the volume of fluid that may be simultaneously exposed UV lamp 86, and thus allow for an increase in the flow rate. For example, the fluid channels 88 may include an approximate spiral, an approximate sine wave, or an approximate "S" curve so as to increase the volume of fluid that may be simultaneously exposed to UV lamp 86. Upper housing 93 further may include reflective coating 87, e.g., a white coating such as ZnO or other diffuse or Lambertian reflector, so as to enhance irradiation of the tubing and shield the patient from potential UV light exposure.

Figure 6B:
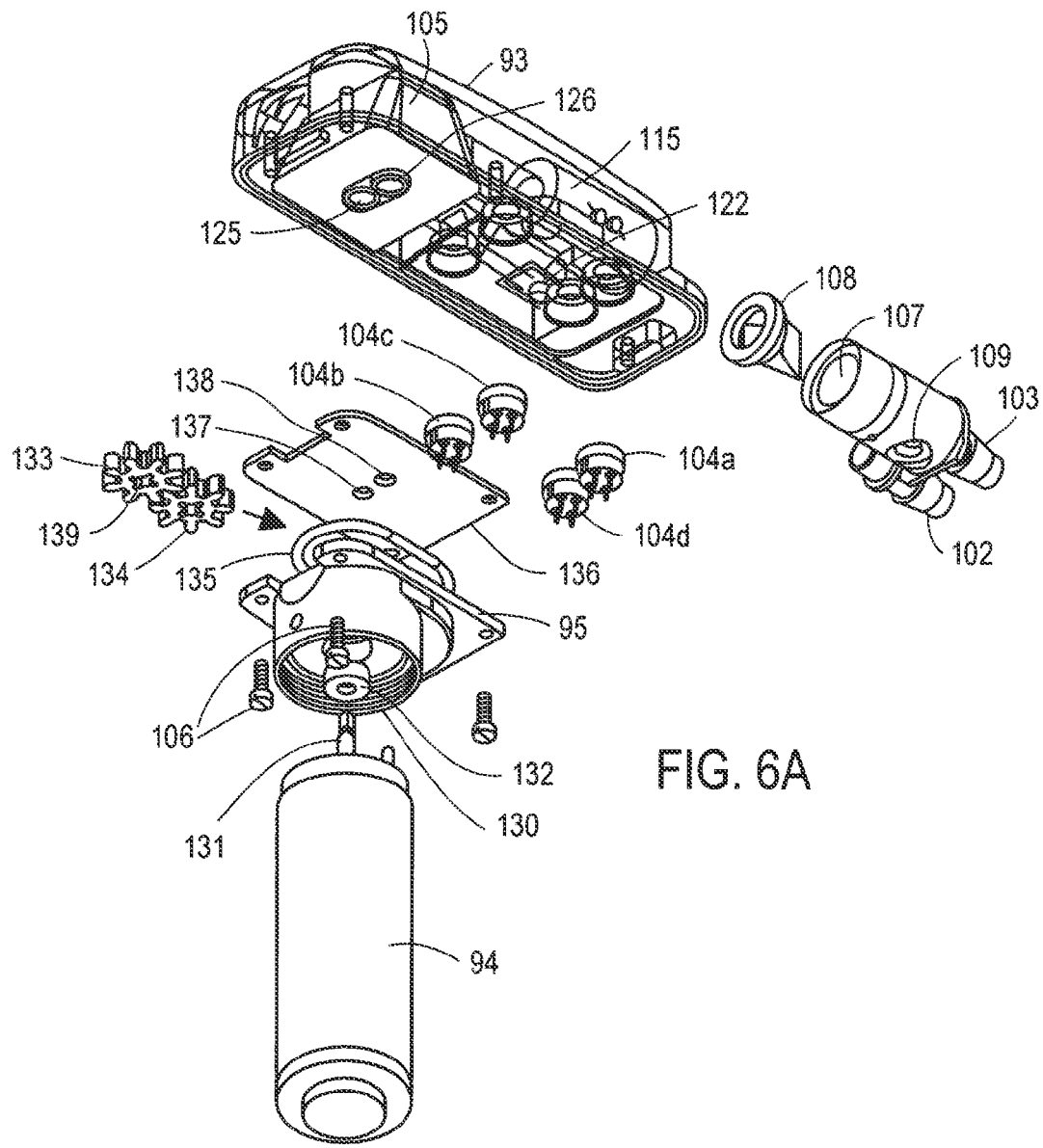
Figure 6B:
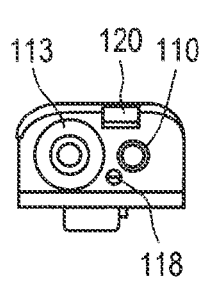

Referring now to FIGS. 6A to 6D, further details of the gear pump and fluid path are described. In FIGS. 6A-6D, like components are identified using the same reference numbers from FIGS. 5A and 5B. FIG. 6A is an exploded view showing assembly of motor 94 with gear pump housing 95 and upper housing 93, as well as the components of the fluid path within the implantable device. Upper housing 93 preferably comprises a high strength plastic or metal alloy material that can be molded or machined to include openings and channels to accommodate inlet nipple 102, outlet nipple 103, pressure sensors 104a-104d, manifold 105 and screws 106. Nipples 102 and 103 preferably are machined from a high strength biocompatible metal alloy, and outlet nipple 103 further includes channel 107 that accepts elastomeric duckbill valve 108. Outlet nipple 103 further includes lateral recess 109 that accepts pressure sensor 104a, which is arranged to measure pressure at the inlet end of the bladder catheter, corresponding to pressure in the patient's bladder (or peritoneal cavity).

Figure 6C:
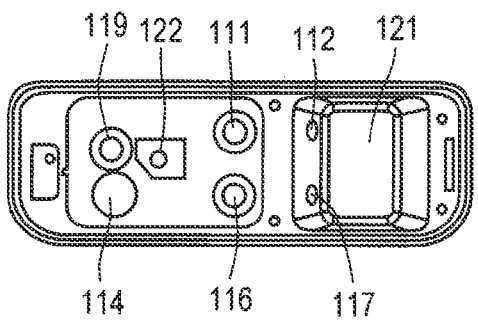

Referring now also to FIGS. 6B and 6C, inlet nipple 102 is disposed within opening 110, which forms a channel in upper housing 93 that includes opening 111 for pressure sensor 104*b* and opening 112 that couples to manifold 105. Pressure sensor 104*b* is arranged to measure the pressure at the outlet end of the peritoneal catheter, corresponding to pressure in the peritoneal cavity. Outlet nipple 103, including duckbill valve 107, is disposed within opening 113 of upper housing 93 so that lateral recess 108 is aligned with opening 114 to permit access to the electrical contacts of pressure sensor 104*a*. Opening 113 forms channel 115 that includes opening 116 for pressure sensor 104*c*, and opening 117 that couples to manifold 105. Upper housing 93 preferably further includes opening 118 that forms a channel including opening 119 for accepting pressure sensor 104*d*. Pressure sensor 104*d* measures ambient pressure, and the output of this sensor is used to calculate differential pressures as described above. Upper housing further includes notch 120 for accepting connector 26 (see FIG. 1A) for retaining the peritoneal and bladder catheters coupled to inlet and outlet nipples 102 and 103. Upper housing 93 further includes recess 121 to accept manifold 105, and peg 122, to which support member 97 (see FIG. 5B) is connected.

Figure 6D:
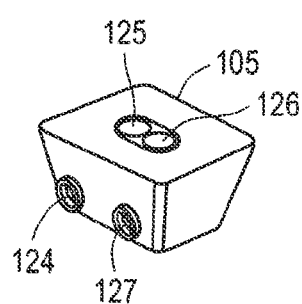

As shown in FIGS. 6A and 6D, manifold 105 preferably comprises a molded elastomeric component having two separate fluid channels (such channels designated 88 in FIG. 5B) that couple inlet and outlet flow paths through upper housing 93 to the gear pump. The first channel includes inlet 124 and outlet 125, while the second channel includes inlet 126 and outlet 127. Inlet 124 couples to opening 112 (see FIG. 6C) of the peritoneal path and outlet 127 couples to opening 117 of the bladder path. Manifold 105 is configured to improve manufacturability of the implantable device, by simplifying construction of upper housing 93 and obviating the need to either cast or machine components with complicated non-linear flow paths. Optional UV lamp 86 and surface 87 (not shown in FIGS. 6A-6D) may be placed in suitable positions within housing 93 and relative to manifold 105 to sufficiently irradiate the fluid as motor 94 pumps the fluid through housing 93.

Figure 7A:
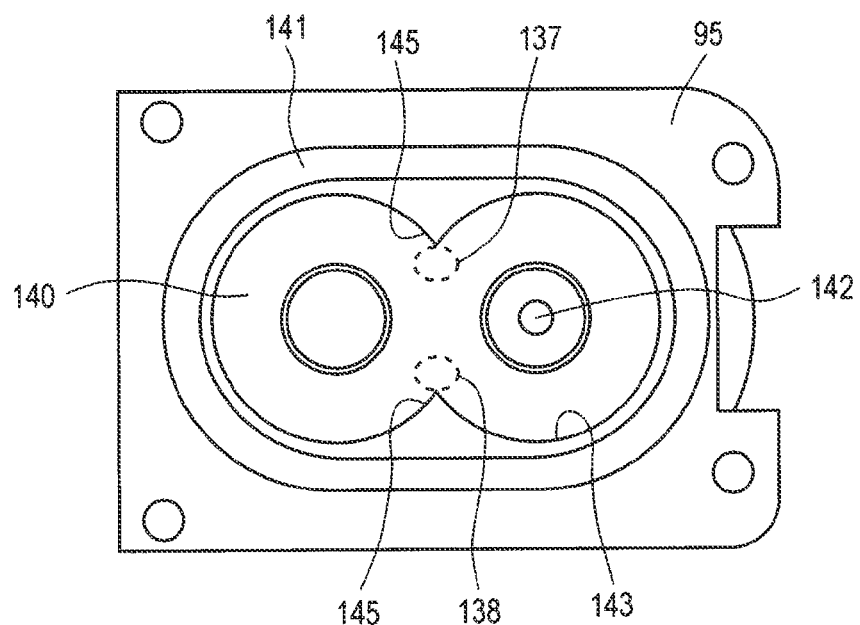
FIGS. 7A and 7B are, respectively, a plan view of the gear pump housing of the implantable device of FIG. 5A, and a plan view of a model of the gear pump constructed in accordance with the principles of the present invention.
Figure 7B:
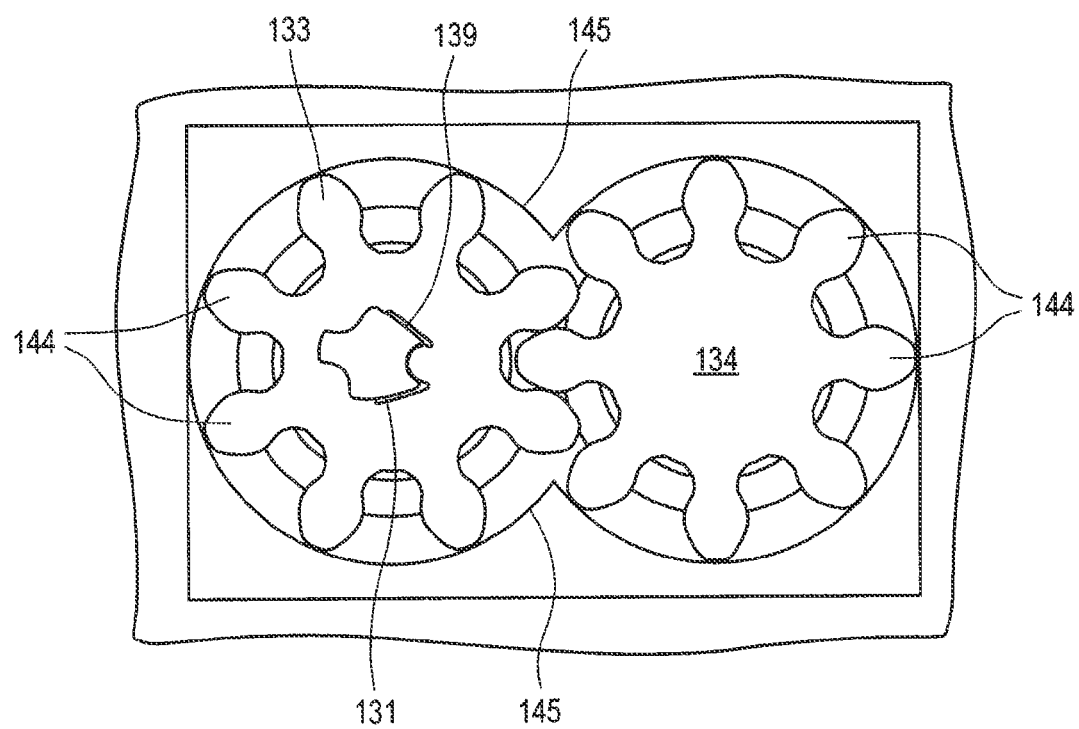

Referring now to FIGS. 6A, 7A and 7B, motor 94 is coupled to gear pump housing 95 using mating threads 130, such that splined shaft 131 of motor 94 passes through bearing 132. The gear pump of the present invention comprises intermeshing gears 133 and 134 enclosed in gear pump housing 95 by O-ring seal 135 and plate 136. The gear pump is self-priming. Plate 136 includes openings 137 and 138 that mate with outlet 125 and inlet 126 of manifold 105, respectively. Splined shaft 131 of motor 94 extends into opening 139 of gear 133 to provide floating engagement with that gear. Interaction of the splined shaft with the gears is described below with respect to FIG. 7B.

FIG. 7A depicts the obverse side of gear pump housing 95 of FIG. 6A, and includes recess 140 that is sized to accept gears 133 and 134, and groove 141 that accepts O-ring seal 135. Gears 133 and 134 are seated within recess 140 such that splined shaft 131 extends through opening 142 and floats within keyed opening 139 of gear 133. Gears 133 and 134 are dimensioned so as to sit within recess 140 with a close tolerance (e.g., 0.2 mm) to wall 143 of the recess, but spin as freely as the viscosity of the fluid permits. Openings 137 and 138 of plate 136 (see FIG. 6A) are positioned over the juncture of gears 133 and 134 (shown in dotted line in FIG. 7A) so that rotation of gear 133 in a clockwise direction (when viewed from above) creates suction that draws fluid into the gear pump housing through opening 137, and expels fluid through opening 138. Likewise, if motor 94 drives gear 133 in a counterclockwise direction (as viewed from above), the gear pump will draw fluid into the gear pump housing through opening 138 and expel it through opening 137, thereby reversing flow.

As depicted in the simplified model of FIG. 7B, gear 134 has no axle, but instead floats freely within its portion of recess 140. Splined shaft 131 engages keyed opening 139 of gear 133, so that gear 133 floats on splined shaft 131. Advantageously, this arrangement improves pump efficiency and manufacturability, and reduces power consumption by motor 94 by reducing the effects of manufacturing variations and thermal effects. In particular, slight variations in motor shaft eccentricity or straightness, resulting from manufacturing tolerances or differential thermal expansion, will not cause the gear to bind against the interior of recess 140 or against gear 134. Instead, different portions of the surfaces of shaft 131 and keyed opening 139 contact one another during revolution of shaft 131 to continuously transmit rotational torque to gear 133. However, energy-wasting forces resulting from shaft eccentricities, variations in manufacturing tolerances or differential thermal expansion of the components are reduced. In addition, this floating arrangement may reduce the risk that particulate matter causes binding between the gears and wall 143, since the gears may move laterally to accommodate such particulate matter.

Gears 133 and 134 include intermeshing lobes 144 that positively displace fluid as they engage and disengage, with substantially no bypass flow. In this manner the volume and viscosity of fluid transported by gears 133 and 134 may computed by tracking the number of motor revolutions sensed by the Hall Effect sensors disposed within motor 94. As further shown in FIGS. 7A and 7B, recess 140 of gear pump housing 95 comprises two interconnected, substantially circular, lobes. This arrangement retains gears 133 and 134 in proper relation to wall 143 of the recess, as well as relative to one another. In a preferred embodiment, cusps 145, formed where the two lobes intersect, are configured to form tangents to radii drawn from the centers of the respective lobes. Advantageously, configuring the cusps in this manner reduces the potential for gears 133 and 134 to impinge upon wall 143.

The Charging and Communication System

Figure 8A:
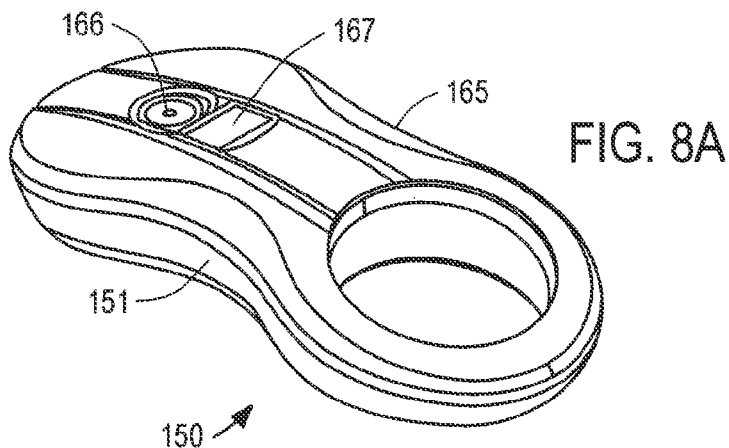
FIGS. 8A and 8B are, respectively, perspective and top views of the handpiece portion of an exemplary charging and communication system of the present invention.
Figure 8B:
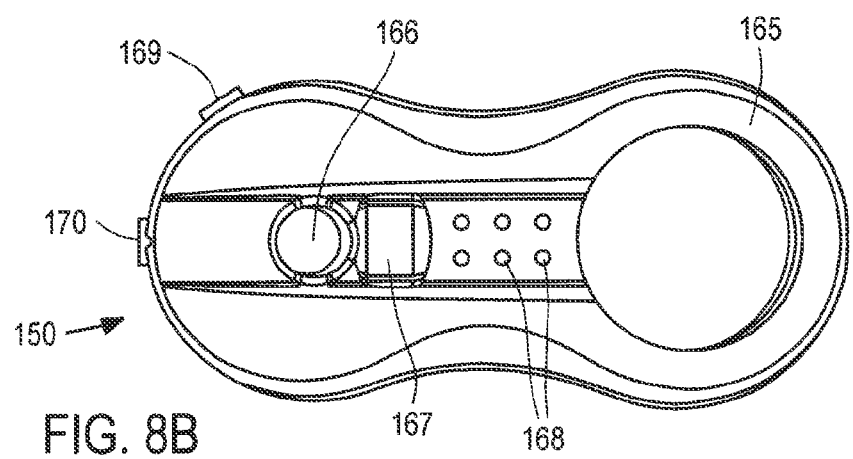
Figure 9:
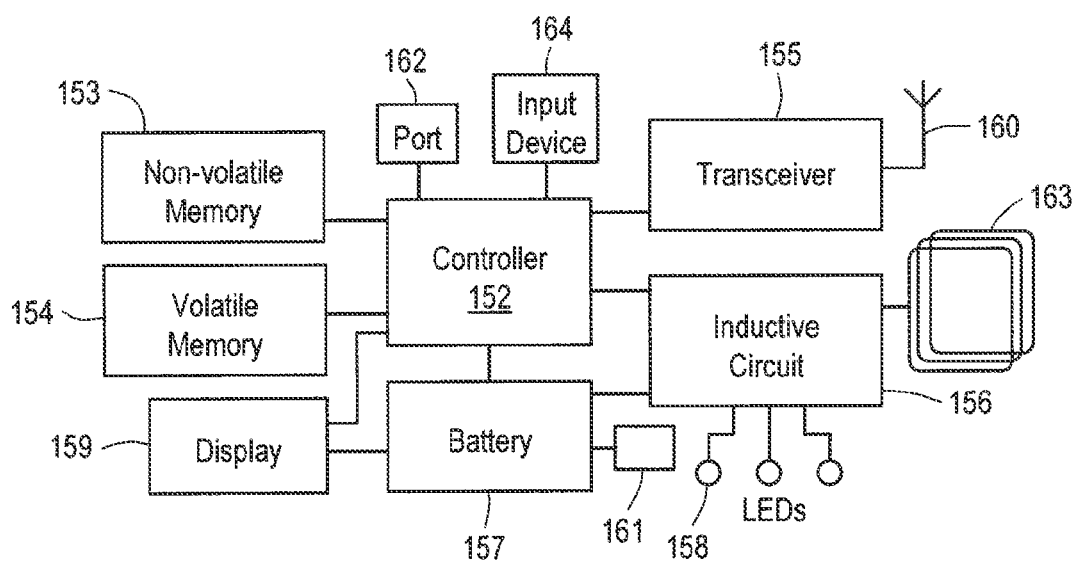
FIG. 9 is a schematic diagram of the electronic components of an exemplary embodiment of the charging and communication system of the present invention.

Referring to FIGS. 8A, 8B and 9, charging and communication system 150 of the present invention (corresponding to system 30 of FIG. 1A) is now described in greater detail. In one preferred embodiment, charging and communication system 150 comprises handpiece 151 and base 31 (see FIG. 1A). Base 31 provides comprises a cradle for recharging handpiece 151, and preferably contains a transformer and circuitry for converting conventional 120V power service to a suitable DC current to charge handpiece 151 when it is coupled to the base. Alternatively, handpiece 151 may include circuitry for charging the handpiece battery, and a detachable power cord. In this embodiment, handpiece 151 may be directly plugged into a convention 120V wall socket for charging, and the power cord removed when the handpiece is used to recharge the implantable device.

As shown in FIG. 9, handpiece 151 contains controller 152, illustratively the processor of a micro-controller unit coupled to nonvolatile memory 153 (e.g., either EEPROM or flash memory), volatile memory 154, radio transceiver 155, inductive circuit 156, battery 157, indicator 158 and display 159. Controller 152, memories 153 and 154, and radio transceiver 155 may be incorporated into a single microcontroller unit, such as the MPS430 family of microprocessors, available from Texas Instruments Incorporated, Dallas, Tex. Transceiver 155 is coupled to antenna 160 for sending and receiving information to implantable device 20. Battery 157 is coupled to connector 161 that removably couples with a connector in base 31 to recharge the battery. Port 162, such as a USB port or comparable wireless circuit, is coupled to controller 152 to permit information to be exchanged between handpiece 151 and the monitoring and control system. Inductive circuit 156 is coupled to coil 163. Input device 164, preferably a multi-function button, also is coupled to controller 152 to enable a patient to input a limited number of commands. Indicator 158 illustratively comprises a plurality of LEDs that illuminate to indicate the quality of charge coupling achieved between the handpiece and implantable device, and therefore assist in optimizing the positioning of handpiece 151 relative to the implantable device during recharging. In one preferred embodiment, indicator 158 is omitted, and instead a bar indicator provided on display 159 that indicates the quality-of-charging resulting from the coupling of coils 163 and 84.

In a preferred embodiment, handpiece 151 includes a device identifier stored in nonvolatile memory 153 that corresponds to the device identifier stored in nonvolatile memory 71 of the implantable device, such that handpiece 151 will communicate only with its corresponding implantable device 20. Optionally, a configurable handpiece for use in a physician's office may include the ability to interrogate an implantable device to request that device's unique device identifier, and then change the device identifier of the monitoring and control system 40 to that of the patient's implantable device, so as to mimic the patient's handpiece. In this way, a physician may adjust the configuration of the implantable device if the patient forgets to bring his handpiece 151 with him during a visit to the physician's office.

Controller 152 executes firmware stored in nonvolatile memory 153 that controls communications and charging of the implantable device. Controller 152 also is configured to transfer and store data, such as event logs, uploaded to handpiece 151 from the implantable device, for later retransmission to monitoring and control system 40 via port 162, during physician office visits. Alternatively, handpiece 151 may be configured to recognize a designated wireless access point within the physician's office, and to wirelessly communicate with monitoring and control system 40 during office visits. As a further alternative, base 31 may include telephone circuitry for automatically dialing and uploading information stored on handpiece 151 to a physician's website via a secure connection, such as alarm information.

Controller 152 preferably includes a low-power mode of operation and includes an internal clock, such that the controller periodically awakens to communicate with the implantable device to log data or to perform charging functions. Controller 152 preferably is configured to awaken when placed in proximity to the implantable device to perform communications and charging functions, and to transmit commands input using input device 164. Controller 152 further may includes programming for evaluating information received from the implantable device, and generating an alarm message on display 159. Controller 152 also may include firmware for transmitting commands input using input device 164 to the implantable device, and monitoring operation of the implantable device during execution of such commands, for example, during boost or jogging/shaking operation of the gear pump to clear a blockage. In addition, controller 152 controls and monitors various power operations of handpiece 151, including operation of inductive circuit 156 during recharging of the implantable device, displaying the state of charge of battery 74, and controlling charging and display of state of charge information for battery 157.

Nonvolatile memory 153 preferably comprises flash memory or EEPROM, and stores the unique device identifier for its associated implantable device, firmware to be executed by controller 152, configuration set point, and optionally, coding to be executed on transceiver 155 and/or inductive circuit 156. Firmware and set point data stored on nonvolatile memory 153 may be updated using information supplied by control and monitoring system 40 via port 162. Volatile memory 154 is coupled to and supports operation of controller 152, and stores data and event log information uploaded from implantable device 20.

In addition, in a preferred embodiment, nonvolatile memory 153 stores programming that enables the charging and communication system to perform some initial start-up functions without communicating with the monitor and control system. In particular, memory 153 may include routines that make it possible to test the implantable device during implantation using the charging and communication system alone in a "self-prime mode" of operation. In this case, a button may be provided that allows the physician to manually start the pump, and display 159 is used to provide feedback whether the pumping session was successful or not. Display 159 of the charging and communication system also may be used to display error messages designed to assist the physician in adjusting the position of the implantable device or peritoneal or bladder catheters. These functions preferably are disabled after the initial implantation of the implantable device.

Transceiver 155 preferably comprises a radio frequency transceiver, e.g., conforming to the Bluetooth or IEEE 802.11 wireless standards, and is configured for bi-directional communications via antenna 160 with transceiver circuit 76 disposed in the implantable device. Transceiver 155 also may include a low power mode of operation, such that it periodically awakens to listen for incoming messages and responds only to those messages including the unique device identifier assigned to its associated implantable device. Transceiver 155 preferably employs an encryption routine to ensure that messages sent to, or received from, the implantable device cannot be intercepted or forged.

Inductive circuit 156 is coupled to coil 163, and is configured to inductively couple with coil 84 of the implantable device to recharge battery 74 of the implantable device. In one embodiment, inductive circuit 156 is coupled to indicator 158, preferably a plurality of LEDs that light to indicate the extent of magnetic coupling between coils 163 and 84 (and thus quality of charging), thereby assisting in positioning handpiece 151 relative to the implantable device. In one preferred embodiment, inductive coils 84 and 163 are capable of establishing good coupling through a gap of 35 mm, when operating at a frequency of 315 kHz or less. In an embodiment in which implantable device includes optional infrared LED 83, charging and communication system 30 may include an optional infrared sensor (not shown) which detects that infrared light emitted by LED 83 and further assists in positioning handpiece 151 to optimize magnetic coupling between coils 163 and 84, thereby improving the energy transmission to the implantable device.

In accordance with one aspect of the present invention, controller 152 may be configured to periodically communicate with the implantable device to retrieve temperature data generated by temperature sensor 78 and stored in memory 72 during inductive charging of battery 74. Controller 152 may include firmware to analyze the battery temperature, and to adjust the charging power supplied to inductive circuit 163 to maintain the temperature of the implantable device below a predetermined threshold, e.g., less than 2° C. above body temperature. That threshold may be set to reduce thermal expansion of the battery and surrounding electronic and mechanical components, for example, to reduce thermal expansion of motor and gear pump components and to reduce the thermal strain applied to the seal between lower portion 92 of housing and upper housing 93. In a preferred embodiment, power supplied to inductive coil 163 is cycled between high power (e.g., 120 mA) and low power (e.g., 40 mA) charging intervals responsive to the measured temperature within the implantable device.

As discussed above with respect to inductive circuit 75 of the implantable device, inductive circuit 156 optionally may be configured to transfer additional power to motor 73 of the implantable device, via inductive circuit 75 and battery 74, in a "boost" mode or jogging mode to unblock the gear pump. In particular, if an alarm is transmitted to controller 152 that motor 73 is stalled, e.g., due to a block created by ascitic fluid, the patient may be given the option of using input device 164 to apply an overvoltage to motor 73 from inductive circuit 75 for a predetermined time period to free the blockage. Alternatively, activating input device 164 may cause controller 152 to command processor 70 to execute a routine to jog or shake the gear pump by rapidly operating motor 74 in reverse and forward directions to disrupt the blockage. Because such modes of operation may employ higher energy consumption than expected during normal operation, inductive circuits 156 and 75 may be configured to supply the additional energy for such motor operation directly from the energy stored in battery 157, instead of depleting battery 74 of the implantable device.

Battery 157 preferably comprises a lithium ion or lithium polymer battery capable of long lasting operation, e.g., up to three years. Battery 157 has sufficient capacity to supply power to handpiece 151 to operate controller 152, transceiver 155, inductive circuit 156 and the associated electronics while disconnected from base 31 and during charging of the implantable device. In a preferred embodiment, battery 157 has sufficient capacity to fully recharge battery 74 of the implantable device from a depleted state in a period of about 2-4 hours. Battery 157 also should be capable of recharging within about 2-4 hours. It is expected that for daily operation moving 700 ml of fluid, battery 157 and inductive circuit 156 should be able to transfer sufficient charge to battery 74 via inductive circuit 75 to recharge the battery within about 30 minutes. Battery capacity preferably is supervised by controller 152 using a charge accumulator algorithm.

Referring again to FIGS. 8A and 8B, handpiece 151 preferably includes housing 165 having multi-function button 166 (corresponding to input device 164 of FIG. 9) and display 167 (corresponding to display 159 of FIG. 9). Plurality of LEDs 168 is disposed beneath a translucent portion of handpiece 151, and corresponds to indicator 158 of FIG. 9. Port 169 enables the handpiece to be coupled to monitoring and control system 40 (and corresponds to port 162 of FIG. 9), while connector 170 (corresponding to connector 161 in FIG. 9) permits the handpiece to be coupled to base 31 to recharge battery 157. Multi-function button 166 provides the patient the ability to input a limited number of commands to the implantable device. Display 167, preferably an OLED or LCD display, provides visible confirmation that a desired command input using multifunction button 166 has been received. Display 167 also may display the status and state of charge of battery 74 of the implantable device, the status and state of charge of battery 157 of handpiece 151, signal strength of wireless communications, quality-of-charging, error and maintenance messages. Inductive coil portion 171 of housing 165 houses inductive coil 163.

LEDs 168 are visible through the material of housing 165 when lit, and preferably are arranged in three rows of two LEDs each. During charging, the LEDs light up to display the degree of magnetic coupling between inductive coils 163 and 84, e.g., as determined by energy loss from inductive circuit 156, and may be used by the patient to accurately position handpiece 151 relative to the implantable device. Thus, for example, a low degree of coupling may correspond to lighting of only two LEDs, an intermediate degree of coupling with lighting of four LEDs, and a preferred degree of coupling being reflected by lighting of all six LEDs. Using this information, the patient may adjust the position of handpiece 151 over the area where implantable device is located to obtain a preferred position for the handpiece, resulting in the shortest recharging time. In one preferred embodiment, LEDs 168 are replaced with an analog bar display on display 167, which indicates the quality of charge coupling.

The Monitoring and Control System

Figure 10:
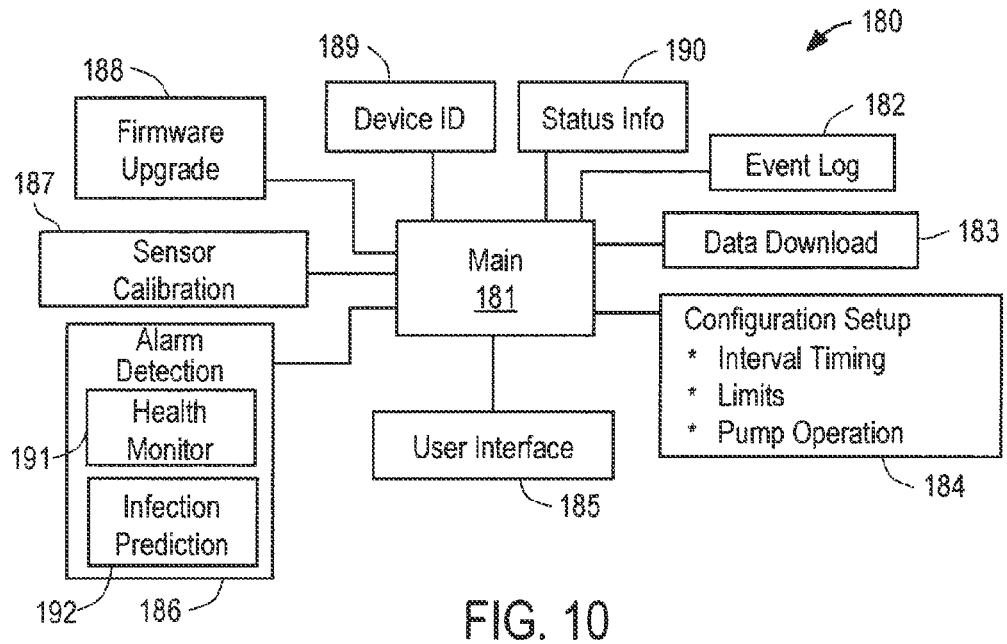
FIG. 10 is a schematic diagram of the functional components of the monitoring and control software employed in an exemplary embodiment of the artificial liver system of the present invention.

Turning to FIG. 10, the software implementing monitoring and control system of FIG. 1A will now be described. Software 180 comprises a number of functional blocks, schematically depicted in FIG. 10, including main block 184, event logging block 182, data download block 183, configuration setup block 184, user interface block 185, alarm detection block 186 including health monitor block 191 and infection prediction block 192, sensor calibration block 187, firmware upgrade block 188, device identifier block 189 and status information block 190. The software preferably is written in C++ and employs an object oriented format. In one preferred embodiment, the software is configured to run on top of a Microsoft Windows® (a registered trademark of Microsoft Corporation, Redmond, Wash.) or Unix-based operating system, such as are conventionally employed on desktop and laptop computers. The computer running monitoring and control system software 180 preferably includes a data port, e.g., USB port or comparable wireless connection, that permits handpiece 151 of the charging and communication system to be coupled via port 169. Alternatively, as discussed above, the computer may include a wireless card, e.g., conforming to the IEEE 802.11 standard, thereby enabling handpiece 151 to communicate wirelessly with the computer running software 180. As a further alternative, the charging and communication system may include telephony circuitry that automatically dials and uploads data, such as alarm data, from handpiece 151 to a secure website accessible by the patient's physician.

Main block 184 preferably consists of a main software routine that executes on the physician's computer, and controls overall operation of the other functional blocks. Main block 184 enables the physician to download event data and alarm information stored on handpiece 151 to his office computer, and also permits control and monitoring software 180 to directly control operation of the implantable device when coupled to handpiece 151. Main block also enables the physician to upload firmware updates and configuration data to the implantable device.

Event Log block 182 is a record of operational data downloaded from the implantable device via the charging and communication system, and may include, for example, pump start and stop times, motor position, sensor data for the peritoneal cavity and bladder pressures, patient temperature, respiratory rate or fluid temperature, pump outlet pressure, humidity, pump temperature, battery current, battery voltage, battery status, and the like. The event log also may include the occurrence of events, such as pump blockage, operation in boost or jog modes, alarms or other abnormal conditions.

Data Download block 183 is a routine that handles communication with handpiece 151 to download data from volatile memory 154 after the handpiece is coupled to the computer running monitoring and control software 180. Data Download block 183 may initiates, either automatically or at the instigation of the physician via user interface block 185, downloading of data stored in the event log.

Configuration Setup block 184 is a routine that configures the parameters stored within nonvolatile memory 71 that control operation of the implantable device. The interval timing parameters may determine, e.g., how long the processor remains in sleep mode prior to being awakened to listen for radio communications or to control pump operation. The interval timing parameters may control, for example, the duration of pump operation to move fluid from the peritoneum to the bladder and the interval between periodic tick movements that inhibit blockage of the implantable device and peritoneal and bladder catheters. Interval timing settings transmitted to the implantable device from monitoring and control software 180 also may determine when and how often event data is written to nonvolatile memory 71, and to configure timing parameters used by the firmware executed by processor 152 of handpiece 151 of the charging and communication system. Block 184 also may be used by the physician to configure parameters stored within nonvolatile memory 71 relating to limit values on operation of processor 70 and motor 73. These values may include minimum and maximum pressures at the peritoneal and bladder catheters, the maximum temperature differential during charging, times when the pump may and may not operate, etc. The limit values set by block 184 also configure parameters that control operation of processor 152 of handpiece 151. Block 184 also may configure parameters store within nonvolatile memory 71 of the implantable device relating to control of operation of processor 70 and motor 73. These values may include target daily volumes of fluid to transport, volume of fluid to be transported per pumping session, motor speed and duration per pumping session. Block 184 also may specify the parameters of operation of motor 73 during boost mode of operation, when coupled to handpiece 151, and shake/jog modes of operation when the implantable device is run using battery 74 alone. Such parameters may include motor speed and voltage, duration/number of revolutions of the motor shaft when alternating between forward and reverse directions, etc.

User interface block 185 handles display of information retrieved from the monitoring and control system and implantable device via data download block 183, and presents that information in an intuitive, easily understood format for physician review. As described below with respect to FIGS. 11 to 15, such information may include status of the implantable device, status of the charging and control system, measured pressures, volume of fluid transported per pumping session or per day, etc. User interface block 185 also generates user interface screens that permit the physician to input information to configure the interval timing, limit and pump operation parameters discussed above with respect to block 184.

Alarm detection block 186 may include a routine for evaluating the data retrieved from the implantable device or charging and communication system, and flagging abnormal conditions for the physician's attention. For example, alarm detection block 186 may include health monitor block 191, which is configured to alert the physician to any changes in the patient's health that may warrant changing the volume, time, and/or frequency with which the dialysate is provided to the patient's peritoneum. For example, if data provided by the implantable device 20 indicate a buildup of toxins or waste products, then the physician may increase the volume, time, and/or frequency with which the dialysate is provided to and withdrawn from the patient's peritoneum. Or, if data provided by the implantable device 20 indicate a relatively low volume of toxins or waste products, then the physician may decrease the volume, time, and/or frequency with which the dialysate is provided to and withdrawn from the patient's peritoneum.

Alarm detection block 186 also, or alternatively, may include infection prediction block 192, which is configured to predict or detect infection based on, for example, one or more of an increase in the patient's temperature above a predefined threshold, an increase in the patient's respiratory rate above a predefined threshold, and/or an increase in the fluid above a predefined threshold. Such flags may be communicated to the physician by changing status indicators presented by user interface block 185, or by displaying to the physician specific information about increases in the patient's temperature, respiratory rate, or fluid viscosity via user interface block 185.

Sensor calibration block 187 may include a routines for testing or measuring drift, of sensors 70, 78-81 employed in the implantable device, e.g., due to aging or change in humidity. Block 187 may then compute offset values for correcting measured data from the sensors, and transmit that information to the implantable device for storage in nonvolatile memory 71. For example, pressure sensors 104$a$-104$d$ may experience drift due to aging or temperature changes. Block 187 accordingly may compute offset values that are then transmitted and stored in the implantable device to account for such drift.

Firmware upgrade block 188 may comprise a routine for checking the version numbers of the processor or motor controller firmware installed on the implantable device and/or processor firmware on charging and communication system, and identify whether upgraded firmware exists. If so, the routine may notify the physician and permit the physician to download revised firmware to the implantable device for storage in nonvolatile memory 71 or to download revised firmware to the charging and communication system for storage in nonvolatile memory 153.

Device identifier block 189 consists of a unique identifier for the implantable device that is stored in nonvolatile memory 71 and a routine for reading that data when the monitoring and control system is coupled to the implantable device via the charging and communication system. As described above, the device identifier is used by the implantable device to confirm that wireless communications received from a charging and communication system are intended for that specific implantable device. Likewise, this information is employed by handpiece 151 of the charging and communication system in determining whether a received message was generated by the implantable device associated with that handpiece. Finally, the device identifier information is employed by monitoring and control software 180 to confirm that the handpiece and implantable device constitute a matched set.

Status information block 190 comprises a routine for interrogating implantable device, when connected via handpiece 151, to retrieve current status date from the implantable device, and/or handpiece 151. Such information may include, for example, battery status, the date and time on the internal clocks of the implantable device and handpiece, version control information for the firmware and hardware currently in use, and sensor data.

Figure 11:
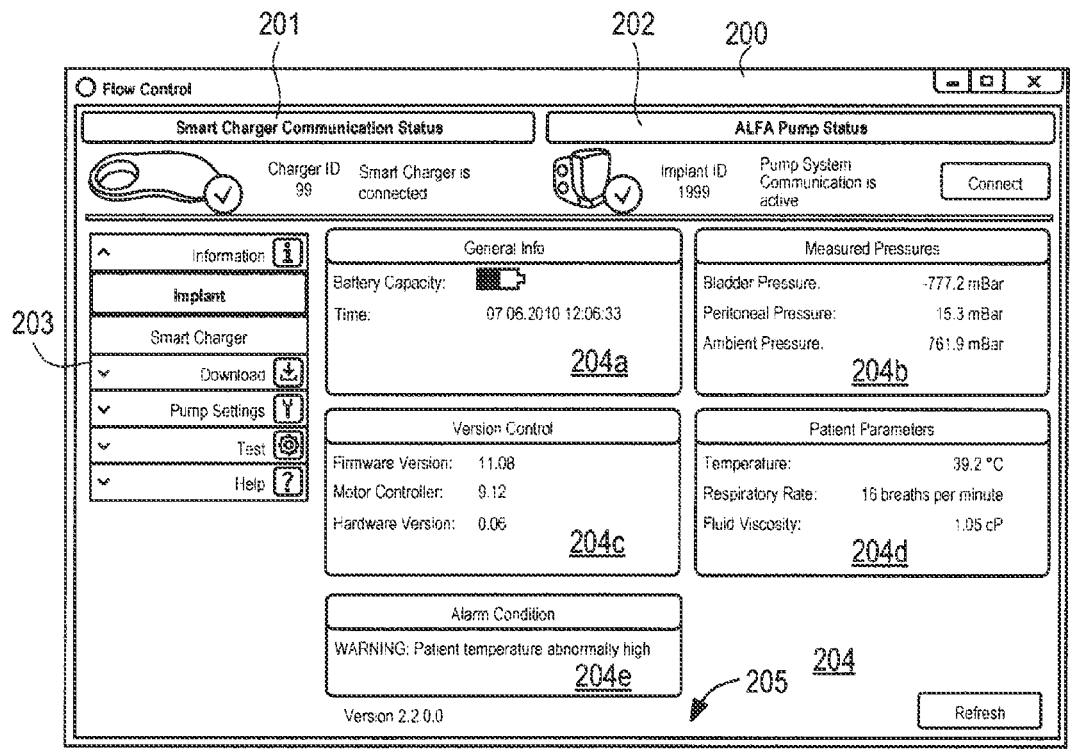
FIGS. 11-15 are exemplary screenshots illustrating various aspects of the user interface of the monitoring and control system of the present invention.

Referring now to FIGS. 11-15, exemplary screen shots generated by user interface block 187 of software 180 are described for an ascites treatment system. FIG. 11 shows main screen 200 that is displayed to a physician running monitoring and control software 180. Main screen 200 includes a status area that displays status information retrieved from the implantable device and the charging and communication system by the routine corresponding to block 190 of FIG. 10. More particularly, the status area includes status area 201 for the charging and communication system (referred to as the "Smart Charger) and status area 202 for the implantable device (referred to as the "ALFA Pump"). Each status area includes an icon showing whether the respective system is operating properly, indicated by a checkmark, the device identifier for that system, and whether the system is connected or active. If a parameter is evaluated by the alarm detection block 186 to be out of specification, the icon may instead include a warning symbol. Menu bar 203 identifies the various screens that the physician can move between by highlighting the respective menu item. Workspace area 204 is provided below the status area, and includes a display that changes depending upon the menu item selected. Below workspace area 204, navigation panel 205 is displayed, which includes the version number of software 180 and a radio button that enables the displays in workspace area 204 to be refreshed.

In FIG. 11, the menu item "Information" with submenu item "Implant" is highlighted in menu bar 203. For this menu item selection, workspace area 204 illustratively shows, for the implantable device, battery status window 204a, measured pressures window 204b and firmware version control window 204c. Battery status window 204a includes an icon representing the charge remaining in battery 74, and may be depicted as full, three-quarters, one-half, one-quarter full or show an alarm that the battery is nearly depleted. The time component of window 204a indicates the current time as received from the implantable device, where the date is expressed in DD/MM/YYYY format and time is expressed in HR/MIN/SEC format based on a 24 hour clock. Measured pressures window 204b displays the bladder pressure, peritoneal pressure and ambient pressures in mBar measured by sensors 104a, 104b and 104d respectively (see FIG. 6A). Version control window 204c indicates the firmware version for processor 70, for the motor controller, and the hardware version of the implantable device. Patient parameters window 204d displays the patient's temperature, respiratory rate, and fluid viscosity. Note that if implantable device included other types of sensors, e.g., sensors that measure the levels of toxins and/or waste products in the fluid, then the parameters measured by such sensors could also be displayed in window 204d.

Alarm condition window 204e displays any changes in parameters that may indicate a change in the patient's health, such as the possible development of an infection or an improvement or worsening of the patient's liver health (Blocks 191 and 192 in FIG. 10). For example, as illustrated, alarm condition window 204e may alert the physician that the patient's temperature is abnormally high, so that the physician then may follow up with the patient regarding the possibility of infection. In some embodiments, based on information displayed in windows 204b, 204d, and/or 204e, the physician may adjust the operating parameters of the pump, e.g., using the interface described further below with reference to FIG. 14.

Figure 12:
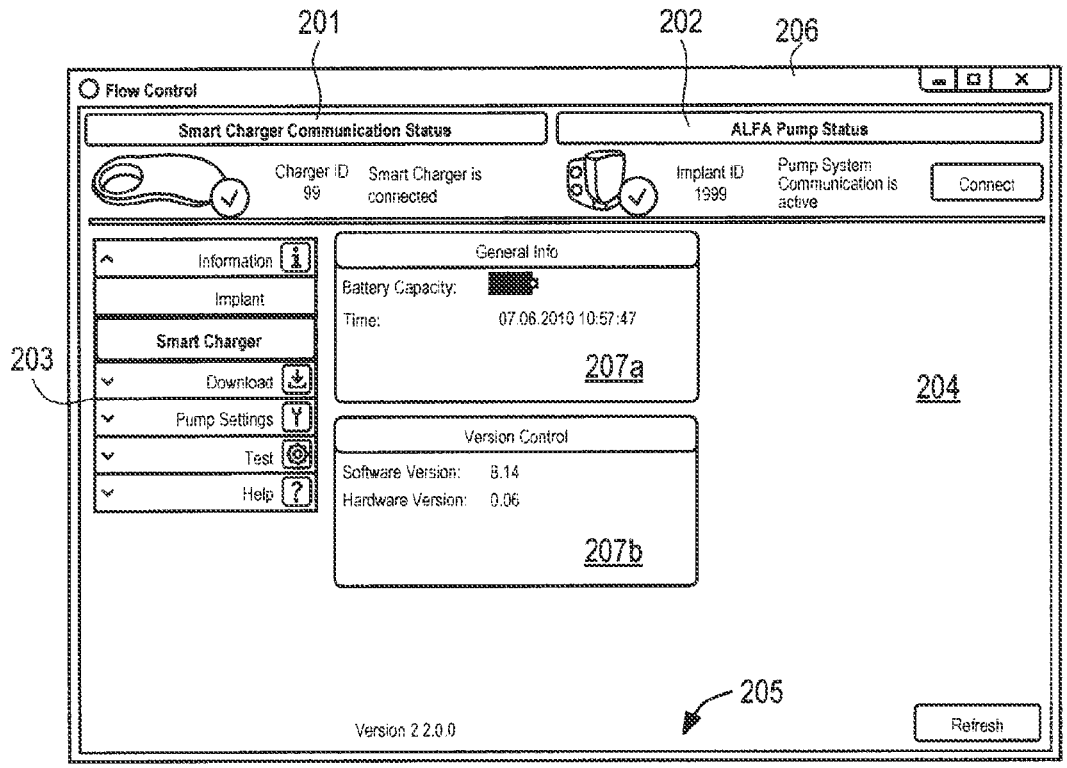

Turning to FIG. 12, screen display 206 corresponding to selection of the "Smart Charger" submenu item in FIG. 11 is described. FIG. 12 includes status area 201 for the charging and communication system, status area 202 for the implantable device, menu bar 203, workspace area 204, and navigation panel 205 as discussed above with respect to FIG. 11. Screen display 206 differs from screen display 200 in that the "Smart Charger" submenu item is highlighted, and workspace area 204 displays, for the charging and control system, battery status window 207a and version control window 207b. Battery status window 207a includes an icon representing the charge remaining in battery 157, and may be depicted as full, three-quarters, one-half, one-quarter full or show an alarm that the battery is nearly depleted. The time component of window 207a indicates the current time as received from handpiece 151, where the date is expressed in DD/MM/YYYY format and time is expressed in HR/MIN/SEC format based on a 24 hour clock. Version control window 207b indicates the firmware version for processor 152, and the hardware version of the charging and control system.

Figure 13:
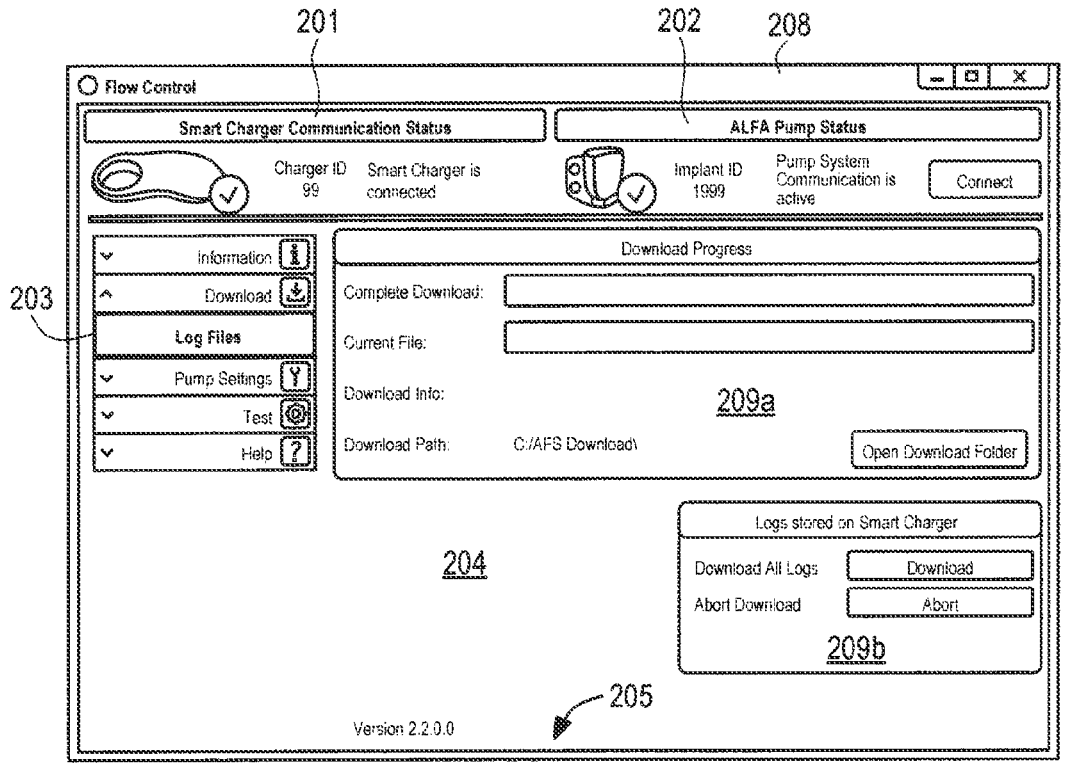

Referring now to FIG. 13, screen display 208 corresponding to selection of the "Download" menu item in FIG. 11 and "Log Files" submenu item is described, and implements the functionality of block 183 of software 180. FIG. 13 includes status area 201 for the charging and communication system, status area 202 for the implantable device, menu bar 203, workspace area 204, and navigation panel 205, all as discussed above. Screen display 208 differs from the "Information" screen display in that the "Log Files" submenu item is highlighted, and workspace area 204 displays download progress window 209a and storage path window 209b. Window 209a includes the path for the directory to which event logs may be downloaded from the implantable device via the charging and communication system. Window 209a also includes an "Open Download Folder" radio button that allows the physician to choose the directory path to which the event logs are downloaded, and a progress bar that is updated to reflect the amount of data downloaded. Window 209b includes a radio button that can be activated to download the event log to the path specified in window 209a, and also includes an "Abort" radio button to interrupt the download process.

Figure 14:
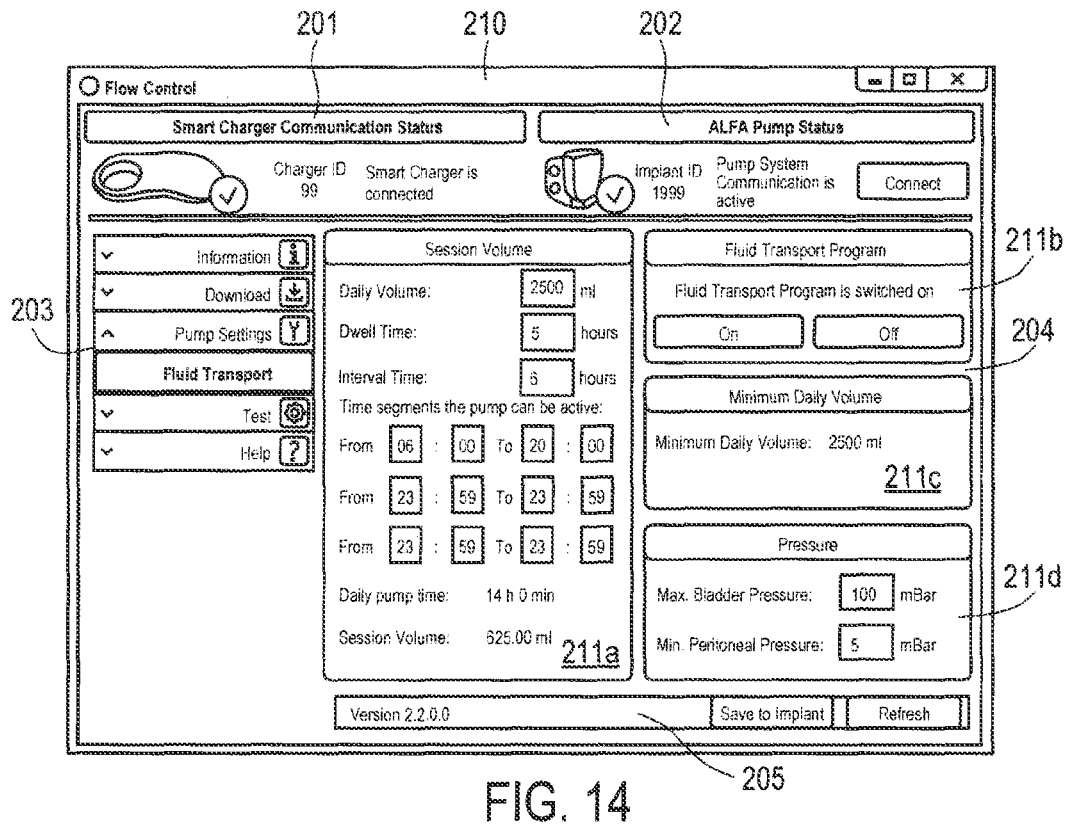

FIG. 14 is an exemplary depiction of screen display 210, corresponding to selection of the "Pump Settings" menu item in FIG. 11 and "Fluid Transport" submenu item, and implements the functionality of blocks 184 and 190 of software 180. FIG. 14 includes status area 201 for the charging and communication system, status area 202 for the implantable device, menu bar 203, workspace area 204, and navigation panel 205, all as discussed above. Screen display 210 differs from the "Information" screen displays in that the "Fluid Transport" submenu item is highlighted, and workspace area 204 includes session volume window 211a, fluid transport program window 211b, minimum daily volume window 211c, pressure window 211d, and a radio button in navigation panel 205 that permits values entered in windows 211a, 211b and 211d to be transmitted and stored in non-volatile memory 71 of the implantable device.

Session volume window 211a displays the current setting for the maximum daily volume to be pumped by the implantable device, the interval time between pumping sessions, the times of the day that the pump may be activated, the total daily pump time and the session volume per pumping session. The maximum daily volume displayed in window 211*a* corresponds to the upper limit of fluid that the pump will transfer to peritoneum and/or to the bladder in a 24-hour period, although the actual volume pumped may be lower if the implantable device detects low fluid conditions. The physician may initially set this value based on perceived patient health, and the value may have an allowed range, e.g., of 20 ml to 4000 ml. The dwell time displayed in window 211*a* allows the physician to set the amount of time that peritoneal dialysate is to remain in the peritoneum. The interval time displayed in window 211*a* allows the physician to set the frequency with which peritoneal dialysate is pumped into the peritoneum to the bladder (as well as from the reservoir to the peritoneum). The daily volume and interval times are used by the configuration setup routine (block 184 of FIG. 10) to compute the session volume, which preferably is in a range of 500 ml to 2,500 ml. The time segments that the pump may be active, displayed in window 211*a*, optionally may be used define the timeframes during which the implantable device can actively move fluid to the bladder; outside of these time segments, the implantable device will not move fluid but may implement the pump tick operation described above to turn the gears on a regular basis to prevent clogging of the gears. Depending on the perceived health of the patient, the physician may set the time segments such that the pump may operate at all hours of the day or night, as preservation of health may override convenience in some circumstances. The daily pump time displayed in window 211*a* is shown in read-only format because it is the aggregate of the time segments entered in the time segments boxes. Finally, the session volume displayed in window 211*a* is computed by block 183 as the amount of fluid transferred to the bladder in a single pumping session.

Fluid transport program window 211*b* displays the status of the program controlling operation of the pump of the implantable device based on the parameters set using block 184 of software 180. In case pump activity must be stopped for any reason, the fluid transport program can be stopped by clicking the "Off" button in window 211*b*, which will cause the Pump to stop pumping until it is manually switched back on. In one embodiment, the fluid transport program may switched on again by pressing the "On" button in window 211*b*. Because the implantable device preferably is implanted with the pump turned off, the physician or surgeon may use window 211*b* to turn on the fluid transport program after the implantable device is first implanted.

Minimum daily volume window 211*c* displays the expected amount of fluid to be pumped to the bladder by the implantable device, and is computed by the configuration setup routine as the session volume times the number of sessions per day, based on the length of the prescribed time segments and interval timing input in window 211*a*.

Pressure window 211*d* of FIG. 14 permits the physician to input values of maximum bladder pressure and minimum peritoneal pressure that are used to control operation of the implantable pump. Thus, for example, processor 70 will command motor 73 to cease a current pumping session, or to skip a planned pumping session during the time segments identified in window 211*a*, if the bladder pressure detected by the pressure sensors exceeds the value specified in window 211*d*. Likewise, processor 70 will command motor 73 to cease a current pumping session, or to skip a planned pumping session during the time segments identified in window 211*a*, if the peritoneal pressure detected by the pressure sensors is less than the value specified in window 211*d*. If configured to operate in the above-described manner, the implantable device will neither cause patient discomfort by overfilling the patient's bladder, nor cause the peritoneal cavity to become excessively dry.

Figure 15:
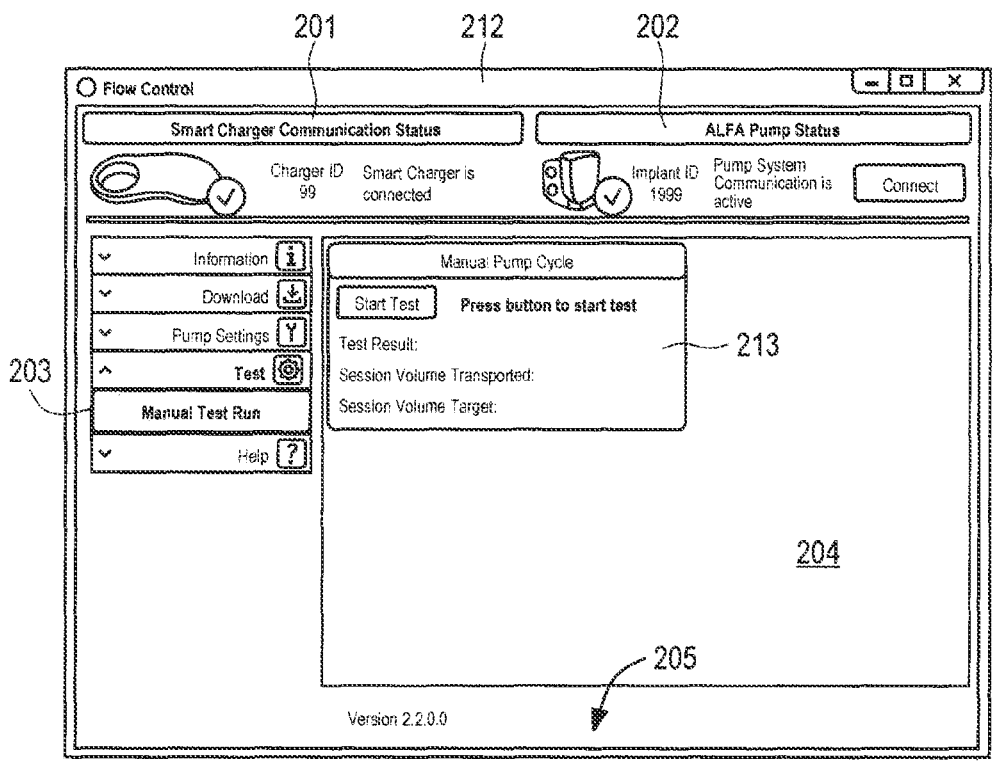

Referring now to FIG. 15, an exemplary depiction of screen display 212, corresponding to selection of the "Test" menu item in FIG. 11 and "Manual Test Run" submenu item is described. FIG. 15 includes status area 201 for the charging and communication system, status area 202 for the implantable device, menu bar 203, workspace area 204, and navigation panel 205, all as discussed above. Screen display 212 differs from the "Information" screen displays in that the "Manual Test Run" submenu item is highlighted, and workspace area 204 includes manual pump cycle window 213. Manual pump cycle window 213 includes radio button "Start Test" which transmits a command to the implantable device via the charging and communication system to cause processor 70 to activate the pump for a predetermined period of time, e.g., a few seconds. Processor 70 receives positional data from the Hall Effect sensors in motor 73 and measured pressure data across pressure sensors 104*c* and 104*d*. Processor 70 computes a session volume and relays that information via the charging and communication system back to software 10, which compares the measured data to a target session volume and provides a test result, e.g., percentage of session target volume achieved or pass/fail icon. The measured session volume, session target volume and test result are displayed in window 213.

While various illustrative embodiments of the invention are described above, it will be apparent to one skilled in the art that various changes and modifications may be made therein without departing from the invention. For example, system 10 may be modified to include additional devices configured to assess the physical and/or mental health of the patient, such as a hand-held biosensor that measures the levels of toxins and/or waste products, e.g., ammonia, c-reactive protein, plasma renin, serum sodium, serum creatinine, prothrombin time, and/or bilirubin, in a drop of the patient's blood. Or, for example, system 10 may be modified to include a hand-held or computer-based device that presents the patient with psychometric tests that measure the psychological health or electrophysiological activity of the subject. Such devices may be configured to wirelessly provide results to monitoring and control system 40 for the physician to use in assessing the patient's health and the possible need to adjust the operating parameters of implantable device 20. The appended claims are intended to cover all such changes and modifications that fall within the true spirit and scope of the invention.

What is claimed:

1. A method of using a fluid management system with a patient having a peritoneum and a bladder, the method comprising:
   introducing a peritoneal dialysis fluid from a reservoir to the patient's peritoneum;
   pumping, using an implantable device, the peritoneal dialysis fluid in the peritoneum to the patient's bladder via a peritoneal catheter and a bladder catheter;
   transferring data from the implantable device to a charging and communication system external to the patient;
   providing the data from the charging and communication system to monitoring and control software running on a computer separate from the charging and communication system; and
   communicating operational parameters from the monitoring and control software to the implantable device via the charging and communication system to control the pumping.

2. The method of claim 1, wherein the implantable device comprises a housing containing a positive displacement gear pump coupled an electric motor and a first controller coupled to a battery, a first transceiver, and a first inductive charging circuit.

3. The method of claim 2, wherein the charging and communication system comprises a second controller coupled to a second transceiver and a second inductive charging circuit and wherein the charging and communication system is configured to wirelessly transfer the data with the implantable device via the first and second transceivers, the method further comprising wirelessly transferring energy from the second inductive circuit to the first inductive circuit to charge the battery.

4. The method of claim 1, wherein the reservoir is configured for external use.

5. The method of claim 4, wherein introducing the peritoneal dialysis fluid further comprises introducing the peritoneal dialysis fluid from the reservoir to the patient's peritoneum using an external pump.

6. The method of claim 4, further comprising providing a belt configured to secure the reservoir to the patient's body.

7. The method of claim 6, wherein the reservoir comprises at least one pouch arranged along the length of the belt.

8. The method of claim 1, wherein the reservoir is configured for internal implantation and comprises a port configured to receive fresh peritoneal dialysis fluid.

9. The method of claim 1, wherein the data comprises measurements of at least one of: respiratory rate, fluid temperature, fluid viscosity, fluid pressure in the peritoneum, or fluid pressure in the bladder measured by at least one sensor coupled to the implantable device.

10. The method of claim 1, wherein transferring the data comprises wirelessly downloading the data stored on the implantable device to a memory disposed within the charging and communication system.

11. The method of claim 10, wherein providing the data comprises periodically communicating via the monitoring and control software with the charging and communication system, using either a wired or wireless connection, to retrieve the data stored in the memory.

12. The method of claim 1, further comprising:
detecting a change in the patient's health based on an increase in at least one of a measured respiratory rate, fluid temperature, or fluid viscosity above a predefined threshold; and
displaying information about the detected change in the patient's health on a display of the computer.

13. The method of claim 12, further comprising:
modifying the operational parameters of the implantable device based on the detected change in the patient's health; and
communicating the modified operational parameters from the monitoring and control software to the implantable device via the charging and communication system.

14. The method of claim 13, wherein the modified operational parameters include at least one of: a volume of the peritoneal dialysis fluid, a time period for which the peritoneal dialysis fluid is permitted to remain within the patient's peritoneum, or a frequency with which peritoneal dialysis fluid is removed from the patient's peritoneum to the bladder.

15. The method of claim 12, wherein the detected change in the patient's health is an infection or a change in liver function.

16. The method of claim 1, further comprising exposing the peritoneal dialysis fluid to light from a UV lamp for a sufficient amount of time to inhibit the growth of colonies of one or more pathogens.

17. The method of claim 1, wherein the method is for treating liver failure.

18. The method of claim 1, wherein the pumping comprises moving the fluid during predetermined time periods and in predetermined volumes responsive to the operational parameters communicated by the monitoring and control software.

19. The method of claim 1, further comprising operating the implantable device in a tick mode to reduce potential clogging, substantially without moving fluid.

20. The method of claim 1, further comprising rapidly alternating a motor of the implantable device between forward and reverse directions to unblock a gear pump of the implantable device.

21. The method of claim 1, wherein the peritoneal dialysis fluid comprises albumin.

* * * * *